(12) United States Patent
Wang

(10) Patent No.: US 12,157,918 B2
(45) Date of Patent: Dec. 3, 2024

(54) CLINICAL ASSESSMENT OF CEREBRAL VASOSPASM RISK FOLLOWING ANEURYSMAL SUBARACHNOID HEMORRHAGE

(71) Applicant: University of Kentucky Research Foundation, Lexington, KY (US)

(72) Inventor: Wang-Xia Wang, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 346 days.

(21) Appl. No.: 17/468,439

(22) Filed: Sep. 7, 2021

(65) Prior Publication Data
US 2022/0090201 A1    Mar. 24, 2022

Related U.S. Application Data

(60) Provisional application No. 63/074,974, filed on Sep. 4, 2020.

(51) Int. Cl.
*C12Q 1/6883* (2018.01)
*A61K 31/4422* (2006.01)
*G16B 40/00* (2019.01)

(52) U.S. Cl.
CPC ........ *C12Q 1/6883* (2013.01); *A61K 31/4422* (2013.01); *G16B 40/00* (2019.02); *C12Q 2600/118* (2013.01); *C12Q 2600/158* (2013.01); *C12Q 2600/178* (2013.01)

(58) Field of Classification Search
CPC ............ C12Q 1/6883; C12Q 2600/118; C12Q 2600/158; C12Q 2600/178; G16B 40/00; A61K 31/4422
See application file for complete search history.

(56) References Cited

U.S. PATENT DOCUMENTS

2018/0127828 A1* 5/2018 Belli ................ A61P 25/00
2018/0371047 A1* 12/2018 Ticho .................... C07K 16/26

OTHER PUBLICATIONS

Sebha et al. "Metamorphosis of Subarachnoid Hemorrhage Research: from Delayed Vasospasm to Early Brain Injury," Mol Neurobiol (2011) 43:27-40 (Year: 2011).*
Roa et al. "Preliminary results in the analysis of the immune response after aneurysmal subarachnoid hemorrhage," Scientific Reports (2020) 10:11809, Published: Jul. 16, 2020 (Year: 2020).*
Wang, W-X, et al., A Highly Predictive MicroRNA Panel for Determining Delayed Cerebral Vasospasm Risk Following Aneurysmal Subarachnoid Hemorrhage. Frontiers in Molecular Biosciences. 2021; vol. 8, Art. 657258.
Wang, W-X, et al., MicroRNAs as Biomarkers for Predicting Complications Following Aneurysmal Subarachnoid Hemorrhage. Intl. J. of Molecular Sciences. 2021; 22, 9492.
Wang WX, Fardo DW, Jicha GA, Nelson Pt. A Customized Quantitative PCR MicroRNA Panel Provides a Technically Robust Context for Studying Neurodegenerative Disease Biomarkers and Indicates a High Correlation Between Cerebrospinal Fluid and Choroid Plexus MicroRNA Expression. Mol Neurobiol. 2017;54(10):8191-202.
Wang WX, Visavadiya NP, Pandya JD, Nelson PT, Sullivan PG, Springer JE. Mitochondria-associated microRNAs in rat hippocampus following traumatic brain injury. Exp Neurol. 2015;265:84-93.
Bache S, Rasmussen R, Rossing M, Laigaard FP, Nielsen FC, Moller K. MicroRNA Changes in Cerebrospinal Fluid After Subarachnoid Hemorrhage. Stroke. 2017;48(9):2391-8. doi:10.1161/STROKEAHA.117.017804.
Bache S, Rasmussen R, Wolcott Z, Rossing M, Møgelvang R, Tolnai D et al. Elevated miR-9 in Cerebrospinal Fluid Is Associated with Poor Functional Outcome After Subarachnoid Hemorrhage. Translational Stroke Research. 2020. doi:10.1007/s12975-020-00793-1.
Kikkawa Y, Ogura T, Nakajima H, Ikeda T, Takeda R, Neki H et al. Altered Expression of MicroRNA-15a and Kruppel-Like Factor 4 in Cerebrospinal Fluid and Plasma After Aneurysmal Subarachnoid Hemorrhage. World Neurosurg. 2017;108:909¬16 e3. doi:10.1016/j.wneu.2017.09.008.
Liu D, Han L, Wu X, Yang X, Zhang Q, Jiang F. Genome-wide microRNA changes in human intracranial aneurysms. BMC Neurol. 2014;14:188. doi:10.1186/s12883-014-0188-x.
Lopes KP, Vinasco-Sandoval T, Vialle RA, Paschoal FM, Jr., Bastos V, Bor-Seng-Shu E et al. Global miRNA expression profile reveals novel molecular players in aneurysmal subarachnoid haemorrhage. Sci Rep. 201 8;8(1):8786. doi:10.1038/s41598-018-27078-w.
Lu G, Wong MS, Xiong MZQ, Leung CK, Su XW, Zhou JY et al. Circulating MicroRNAs in Delayed Cerebral Infarction After Aneurysmal Subarachnoid Hemorrhage. J Am Heart Assoc. 2017;6(4). doi:10.1161/JAHA.116.005363.
Powers CJ, Dickerson R, Zhang SW, Rink C, Roy S, Sen CK. Human cerebrospinal fluid microRNA: temporal changes following subarachnoid hemorrhage. Physiol Genomics. 2016;48(5):361-6. doi:10.1152/physiolgenomics.00052.2015.
Pulcrano-Nicolas AS, Proust C, Clarencon F, Jacquens A, Perret C, Roux M et al. Whole-Blood miRNA Sequencing Profiling for Vasospasm in Patients With Aneurysmal Subarachnoid Hemorrhage. Stroke. 2018;49(9):2220-3. doi:10.1161/STROKEAHA.118.021101.
Stylli SS, Adamides AA, Koldej RM, Luwor RB, Ritchie DS, Ziogas J et al. miRNA expression profiling of cerebrospinal fluid in patients with aneurysmal subarachnoid hemorrhage. J Neurosurg. 2017;126(4):1131-9. doi:10.3171/2016.1.JNS151454.

(Continued)

*Primary Examiner* — Jeffrey S Lundgren
*Assistant Examiner* — William Y Lee
(74) *Attorney, Agent, or Firm* — Stites & Harbison PLLC; Mandy Wilson Decker

(57) ABSTRACT

A treatment method for cerebral vasospasm involves determining amounts of let-7b-5p, miR-9-3p, miR-142-3p, miR-15b-5p, miR-17-5p, miR-19b-3p, miR-20a-5p, miR-24-3p, miR-29a-3p, miR-125b-5p, and miR-142-3p in a biological sample obtained from a subject following aneurysmal subarachnoid hemorrhage (aSAH) to identify the subject as having an elevated risk of cerebral vasospasm, and administering a treatment to the subject when the elevated risk of cerebral vasospasm is identified.

15 Claims, 9 Drawing Sheets

(56) References Cited

OTHER PUBLICATIONS

Su XW, Chan AH, Lu G, Lin M, Sze J, Zhou JY et al. Circulating microRNA 132-3p and 324-3p Profiles in Patients after Acute Aneurysmal Subarachnoid Hemorrhage. PLoS One. 2015;10(12):e0144724. doi: 10.1371/journal.pone.0144724.

* cited by examiner

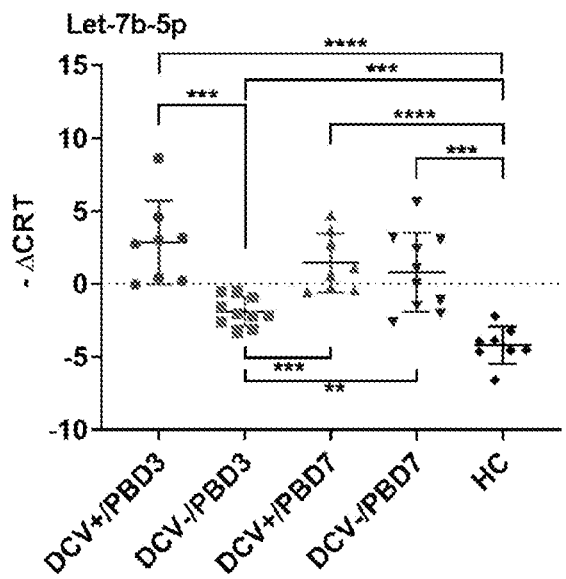
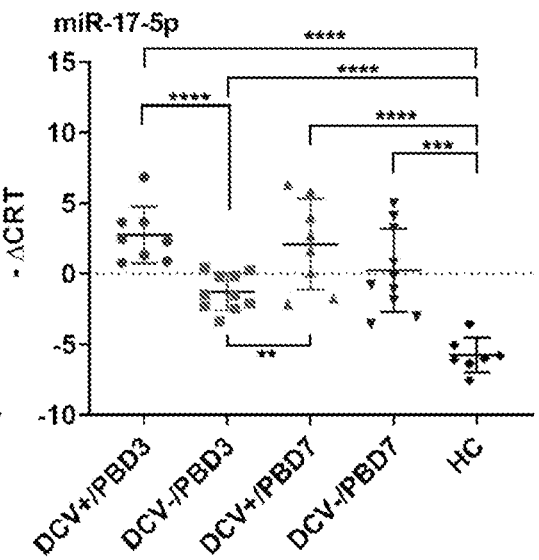
FIG. 1A
FIG. 1B
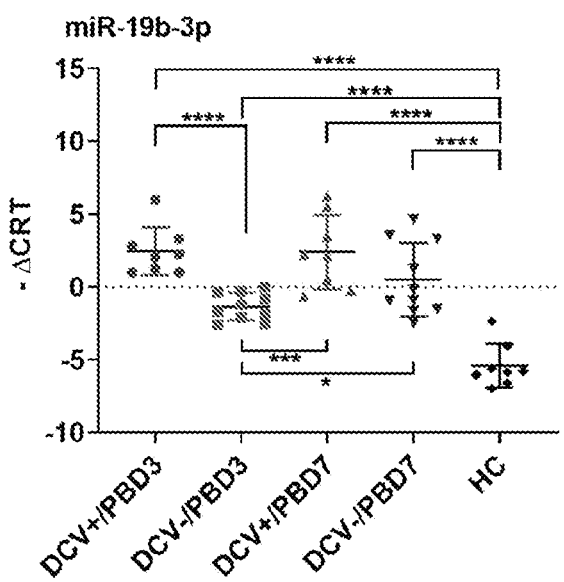
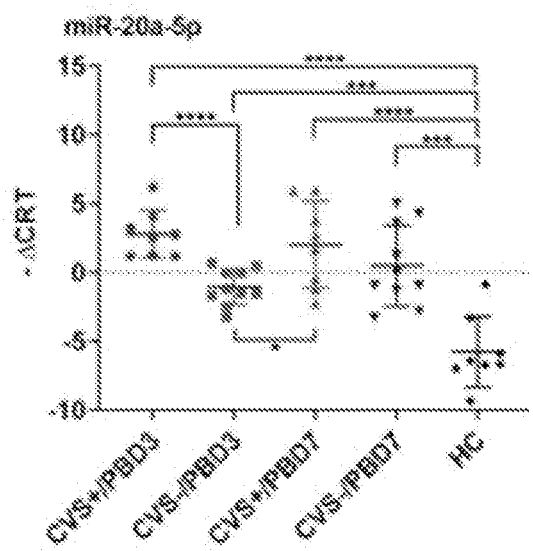
FIG. 1C
FIG. 1D

CLINICAL ASSESSMENT OF CEREBRAL VASOSPASM RISK FOLLOWING ANEURYSMAL SUBARACHNOID HEMORRHAGE

RELATED APPLICATIONS

This application claims priority from U.S. Provisional Application Ser. No. 63/074,974 filed Sep. 4, 2020, the entire disclosure of which is incorporated herein by this reference.

GOVERNMENT INTEREST

This invention was made with government support under grant number P30 AG280303 awarded by the National Institutes of Health. The government has certain rights in the invention.

TECHNICAL FIELD

The presently-disclosed subject matter generally relates to cerebral vasospasm (CVS), also known in the art as delayed cerebral vasospasm (DCV), following aneurysmal subarachnoid hemorrhage (aSAH). In particular, certain embodiments of the presently-disclosed subject matter relate to methods of detecting miRNAs for use in assessing risk of CVS in aSAH.

INTRODUCTION

Aneurysmal subarachnoid hemorrhage (aSAH) is a catastrophic clinical event occurring in approximately 35,000 Americans every year [1, 2]. aSAH occurs when an intracranial arterial aneurysm ruptures, resulting in the release of oxygenated blood into the subarachnoid space where it mixes with cerebrospinal fluid (CSF) [3]. In some cases, this blood may also penetrate into the brain parenchyma or into the ventricular system, causing additional injury [3, 4]. Approximately 20% of aSAH patients die before or during initial hospitalization, and of those patients who survive, approximately 25% will have secondary neurologic injuries resulting in chronic, lifelong neurologic disabilities [5, 6].

Cerebral vasospasm (CVS), also known in the art as delayed cerebral vasospasm (DCV), has long been considered the most devastating acute complication following aSAH and brain injury [7-9]. Approximately 30% of aSAH patients develop CVS [8]. Secondary complications of CVS range from subtle to permanent neurological deficits and death. CVS most commonly occurs during a wide clinical window (3 to 10 days after aneurysm rupture), requiring frequent neurologic monitoring and rapid, intensive interventions to minimize chronic injury and disability. Unfortunately, the pathological mechanisms leading up to CVS are poorly understood but appear to include a complex, multifactorial and interconnected cascade of events involving calcium dependent and independent vasoconstriction, oxidative stress, endothelial dysfunction, inflammatory responses, apoptosis, autophagy, and altered gene expression [10-16]. Predicting CVS risk before it becomes clinically symptomatic is crucial, because early medical management can be initiated to prevent further brain injury. Unfortunately, no effective biomarker exists to predict or diagnose CVS at a clinical time point when neurologic injury can be prevented [17, 18]. At this time, clinical management includes a "wait and see" approach. Therefore, there is an urgent need to identify methods for clinically assessing cerebral vasospasm risk or susceptibility in order to implement treatment, including preventive or management strategies.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently disclosed subject matter includes a method for assessing risk or susceptibility for cerebral vasospasm (CVS), also known in the art as delayed cerebral vasospasm (DCV), in a subject following aneurysmal subarachnoid hemorrhage (aSAH). In some embodiments, the method involves implementing treatment, including preventive or management strategies, for CVS.

The presently-disclosed subject matter further includes a method for determining amounts of micro-RNA (miRNA) molecules in biological sample from a subject following aneurysmal subarachnoid hemorrhage (aSAH). In some embodiments, the method involves assessing risk of developing CVS in an aSAH subject, i.e., in a subject following aSAH.

MicroRNAs (miRNAs) are small, non-coding RNAs that regulate gene expression post-transcriptionally [19, 20]. MiRNAs regulate all aspects of cellular function, and disruption of miRNA activity contributes to many disease states including neurological diseases such as Alzheimer's disease, stroke, and traumatic brain injury [21-26]. Several studies have demonstrated changes in miRNA levels in cerebral arteries following aSAH and CVS [27-29]. For example, one study [30] reported that over 150 miRNAs were differentially expressed in the aneurysmal tissue when compared to normal arteries. This includes endothelium and vascular smooth muscle-enriched miRNAs (such as the Let-7 family, miR-17, miR-23b, hsa-miR-24-1, miR-143, and miR-145), and miRNAs implicated in modulating vascular smooth muscle cell functions (such as miR-1, miR-10, and miR-125b). MiR-143 plays an important role in controlling vascular smooth muscle phenotype by maintaining or inhibiting smooth muscle cell differentiation [31] and was found to be significantly upregulated in cerebral arteries after aSAH [28]. MicroRNAs are also recognized as powerful regulators of CNS inflammatory responses [32], including inflammation that occurs following stroke and aSAH [33, 34].

It is proposed herein that alterations in the levels of a particular set of miRNAs accurately reflect the pathophysiological events in aSAH patients who develop CVS. The rationale for this is based on the fact that miRNAs are highly sensitive to cellular stimuli and pathophysiological conditions, and that the expression patterns of certain miRNAs in peripheral blood or CSF correlate with clinical outcomes associated with stroke or aSAH [24, 35]. Their functional role and the fact that they can be secreted into extracellular fluids make miRNAs attractive candidates as biomarkers for CVS following aSAH. Moreover, miRNAs in biofluids are highly stable at room temperature, resistant to RNase activity [36] and relatively easy to detect and quantify [37].

The presently-disclosed subject matter includes a method for analyzing a biological sample collected from a subject following aneurysmal subarachnoid hemorrhage (aSAH). The biological sample can be, for example, cerebrospinal fluid or plasma. In some embodiments, the biological sample is obtained from the subject within about 12 hours following aSAH. In some embodiments, the sample is obtained from the subject about one, two, three, four, five, six, seven, eight, nine, or ten days following aSAH.

In some embodiments, the method involves providing the biological sample collected from the subject following aSAH; isolating total RNA from the sample; conducting reverse-transcription of miRNAs in the RNA sample to obtain cDNA; amplifying the cDNA; detecting the cDNA and identifying the miRNA from which the cDNA was transcribed; and determining amounts of at least one, two, three, four, five, six, seven, eight, nine, or ten miRNAs in the biological sample, selected from the group consisting of: let-7b-5p, miR-9-3p, miR-15b-5p, miR-17-5p, miR-19b-3p, miR-20a-5p, miR-24-3p, miR-29a-3p, miR-125b-5p, and miR-142-3p.

In some embodiments, the method also includes determining the amounts of at least one, two, three, four, five, six, seven, eight, nine, or ten additional miRNA in the biological sample, selected from group consisting of: miR-145, ath-miR-159a, miR-183, miR-200a, miR-302c-5p, miR-365, miR-502, miR-542-3p, miR-662, and miR-720.

In some embodiments, the method also includes identifying risk of cerebral vasospasm. In some embodiments, the subject is identified as having an elevated risk of cerebral vasospasm when there are elevated amounts of the miRNAs in the biological sample relative to control. In some embodiments, elevated risk is determined by calculating a risk score of a patient using a statistical model and the microRNA expression levels as input data, and comparing the risk score to one or both of a basal score and a low-risk score, and identifying the subject as having an elevated risk for developing vasospasm when the calculated risk score is higher than the basal score and/or the low-risk score.

In some embodiments, the method also includes administering treatment for cerebral vasospasm, including preventive treatment or management treatment. In some embodiments, the treatment includes administering a hypertension medication to the subject. In some embodiments, the treatment includes administering an intra-arterial injection of a vasodilator to the subject. In some embodiments, the treatment includes administering nimodipine to the subject.

The presently-disclosed subject matter includes a treatment method, which involves determining amounts of at least one, two, three, four, five, six, seven, eight, nine, or ten miRNAs selected from the group consisting of let-7b-5p, miR-9-3p, miR-142-3p, miR-15b-5p, miR-17-5p, miR-19b-3p, miR-20a-5p, miR-24-3p, miR-29a-3p, miR-125b-5p, and miR-142-3p in a biological sample obtained from a subject following aneurysmal subarachnoid hemorrhage (aSAH) to identify the subject as having an elevated risk of cerebral vasospasm when there are elevated amounts of the miRNAs relative to control, and administering a treatment to the subject when the elevated risk of cerebral vasospasm is identified. The biological sample can be, for example, cerebrospinal fluid or plasma.

In some embodiments, the method also includes determining the amounts of at least one, two, three, four, five, six, seven, eight, nine, or ten additional miRNA in the biological sample, selected from group consisting of: miR-145, ath-miR-159a, miR-183, miR-200a, miR-302c-5p, miR-365, miR-502, miR-542-3p, miR-662, and miR-720.

In some embodiments, the treatment includes administering a hypertension medication to the subject. In some embodiments, the treatment includes administering an intra-arterial injection of a vasodilator to the subject. In some embodiments, the treatment includes administering nimodipine to the subject.

The presently-disclosed subject matter includes a device for use in identifying risk of cerebral vasospasm in a subject, which includes a combination of probes, including a probe specific for each of at least one, two, three, four, five, six, seven, eight, nine, or ten miRNAs selected from the group consisting of: let-7b-5p, miR-9-3p, miR-15b-5p, miR-17-5p, miR-19b-3p, miR-20a-5p, miR-24-3p, miR-29a-3p, miR-125b-5p, and miR-142-3p.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIGS. 1A-1F. Individual CSF miRNAs that showed highly differential expression in CVS+, CVS−, and HC groups. The differential miRNA expression levels are expressed as −$\Delta$CRT and a two tailed Student's t-test was used to evaluate differences between groups. Significant levels expressed as: **: $p<0.0001$; *: $p=0.0001$ to 0.001; **: $p=0.001$ to 0.01; *: $p=0.01$ to 0.05

DESCRIPTION OF EXEMPLARY EMBODIMENTS

Figure 1E:
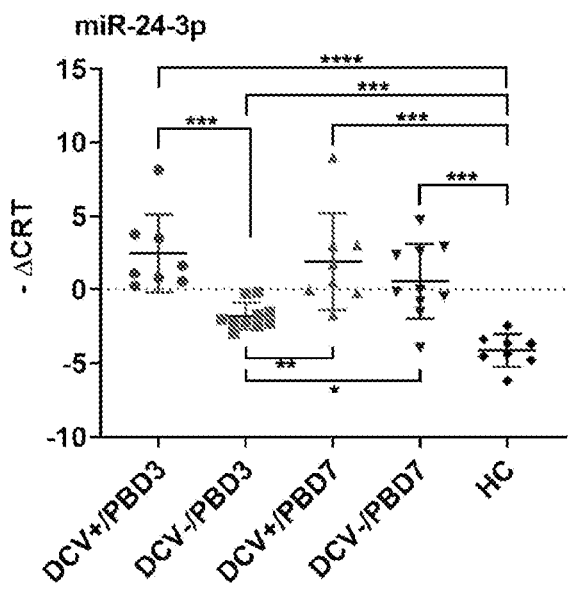

The details of one or more embodiments of the presently-disclosed subject matter are set forth in this document.

Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes a method for determining amounts of micro-RNA (miRNA) molecules in biological sample from a subject following aneurysmal subarachnoid hemorrhage (aSAH). The presently-disclosed subject matter further includes a method for assessing risk of an aSAH subject developing cerebral vasospasm. The presently-disclosed subject matter further includes a method for treating a subject who has been identified as having an elevated risk of cerebral vasospasm.

The presently-disclosed subject matter involves analysis of a biological sample that has obtained from a subject following aSAH. In some embodiments, the sample is obtained from the subject within about 12 hours following aSAH. In some embodiments, the sample is obtained from the subject about one, two, three, four, five, six, seven, eight, nine, or ten days following aSAH. The biological sample can be, for example, a sample comprising cerebrospinal fluid or plasma from the subject.

The presently-disclosed subject matter includes a method for analyzing a biological sample collected from a subject following aneurysmal subarachnoid hemorrhage (aSAH). In some embodiments, the method involves providing the biological sample collected from the subject following aSAH; isolating total RNA from the sample; conducting reverse-transcription of miRNAs in the RNA sample to obtain cDNA; amplifying the cDNA; detecting the cDNA and identifying the miRNA from which the cDNA was transcribed; and determining amounts of at least one, two, three, four, five, six, seven, eight, nine, or ten miRNAs in the biological sample, selected from the group consisting of: let-7b-5p, miR-9-3p, miR-15b-5p, miR-17-5p, miR-19b-3p, miR-20a-5p, miR-24-3p, miR-29a-3p, miR-125b-5p, and miR-142-3p.

In some embodiments, the method also includes determining the amounts of at least one, two, three, four, five, six, seven, eight, nine, or ten additional miRNA in the biological sample, selected from group consisting of: miR-145, ath-miR-159a, miR-183, miR-200a, miR-302c-5p, miR-365, miR-502, miR-542-3p, miR-662, and miR-720.

In some embodiments, the method also includes determining the amounts of one or more additional miRNAs, selected from group consisting of: let-7a, let-7b, let-7c, miR-103, miR-107, miR-124a, miR-1197, miR-125b, miR-1274b, miR-1298, miR-132, miR-142-3p, miR-142-5p, miR-143, miR-146a, miR-146b, miR-150, miR-155, miR-15a, miR-15b, miR-16, miR-17, miR-181a, miR-181c, miR-195, miR-19b, miR-204, miR-20a, miR-21, miR-210-3p, miR-221, miR-223, miR-23a, miR-23b, miR-24, miR-26a, miR-27a, miR-27b, miR-29a, miR-29b, miR-29c, miR-34a, miR-34b, miR-451, miR-484, miR-486-5p, miR-497, miR-520h, miR-553, miR-566, miR-643, miR-874, miR-9-3p, miR-9-5p, miR-92, Cel-miR-39-3p, and U6 snRNA. Methods of detecting miRNA are known in the art and include, for example, quantitative real time polymerase chain reaction (qPCR), miRNA arrays of oligonucleotide probes, RNA sequencing (RNA-seq), and multiplex miRNA profiling assay.

In some embodiments, the method further involves identifying risk of cerebral vasospasm. In some embodiments, the subject is identified as having an elevated risk of cerebral vasospasm when there are elevated amounts of the miRNAs in the biological sample relative to control.

In some embodiments, elevated risk is determined by calculating a risk score of a patient using a statistical model and the amounts of miRNAs as input data, and comparing the risk score to one or both of a basal score and a low-risk score, and identifying the subject as having an elevated risk for developing vasospasm when the calculated risk score is higher than the basal score and/or the low-risk score.

As used herein, the basal score is an established score generated from a group of healthy controls who do not have aSAH or any clinically manifested neurological disease or diagnosis. As used herein, the low-risk score is an established score that is generated from a group of aSAH patients who did not experience cerebral vasospasm.

In some embodiments, the method also includes administering treatment for cerebral vasospasm, including preventive treatment or management treatment. In some embodiments, the treatment includes administering a hypertension medication to the subject. In some embodiments, the treatment includes administering an intra-arterial injection of a vasodilator to the subject. In some embodiments, the treatment includes administering nimodipine to the subject.

The presently-disclosed subject matter further includes a treatment method that involves identifying an elevated risk of cerebral vasospasm, and administering treatment to the subject when the elevated risk of cerebra vasospasm is identified.

In some embodiments, the treatment method involves determining amounts of at least one, two, three, four, five, six, seven, eight, nine, or ten miRNAs selected from the group consisting of let-7b-5p, miR-9-3p, miR-142-3p, miR-15b-5p, miR-17-5p, miR-19b-3p, miR-20a-5p, miR-24-3p, miR-29a-3p, miR-125b-5p, and miR-142-3p in a biological sample obtained from a subject following aneurysmal subarachnoid hemorrhage (aSAH). The biological sample can be, for example, a sample comprising cerebrospinal fluid or plasma.

In some embodiments, the treatment method also includes determining the amounts of at least one, two, three, four, five, six, seven, eight, nine, or ten additional miRNA in the biological sample, selected from group consisting of: miR-145, ath-miR-159a, miR-183, miR-200a, miR-302c-5p, miR-365, miR-502, miR-542-3p, miR-662, and miR-720. In some embodiments, the treatment method also includes determining the amounts of at least one additional miRNA selected from group consisting of: let-7a, let-7b, let-7c, miR-103, miR-107, miR-124a, miR-1197, miR-125b, miR-1274b, miR-1298, miR-132, miR-142-3p, miR-142-5p, miR-143, miR-146a, miR-146b, miR-150, miR-155, miR-15a, miR-15b, miR-16, miR-17, miR-181a, miR-181c, miR-195, miR-19b, miR-204, miR-20a, miR-21, miR-210-3p, miR-221, miR-223, miR-23a, miR-23b, miR-24, miR-26a, miR-27a, miR-27b, miR-29a, miR-29b, miR-29c, miR-34a, miR-34b, miR-451, miR-484, miR-486-5p, miR-497, miR-520h, miR-553, miR-566, miR-643, miR-874, miR-9-3p, miR-9-5p, miR-92, Cel-miR-39-3p, and U6 snRNA.

In some embodiments of the treatment method, the subject can be identified as having an elevated risk of cerebral vasospasm when there are elevated amounts of the miRNAs relative to control. In some embodiments, elevated risk is determined by calculating a risk score of a patient using a statistical model and the amounts of miRNAs as input data, and comparing the risk score to one or both of a basal score and a low-risk score, and identifying the subject as having an elevated risk for developing vasospasm when the calculated risk score is higher than the basal score and/or the low-risk score.

As noted herein, some embodiments of the methods disclosed herein involve administering treatment, including therapeutic and/or preventive treatment, when the subject is identified as having an elevated risk of cerebral vasospasm. As used herein, cerebral vasospasm (CVS) and delayed cerebral vasospasm (DCV) are used interchangeably and refer to a condition known in the art, which involves intracranial vessels spasm resulting in decreased blood flow to brain tissue distal to the site of the spasm. Such decreased blood flow can result in damage to the brain tissue, resulting in permanent neurological deficits or even death.

In some embodiments of the methods disclosed herein, the treatment that is administered is nimodipine. Nimodipine is a calcium channel blocker that has been approved for use in treating cerebral vasospasm.

In some embodiments of the methods disclosed herein, the treatment that is administered is an intra-arterial vasodilator (IAD). For example, intra-arterial nicardipine, verapamil, nitroglycerin, and other known IADs can be used.

In some embodiments, the treatment includes administering a hypertension medication to the subject. Various hypertension medications are known in the art. For example, angiotensin-converting enzyme (ACE) inhibitors can be used, which serves to relax blood vessels. Angiotensin II receptor blockers (ARBs) are another example of hypertension medications, which also serve to relax blood vessels. Calcium channel blockers are also useful in relaxing blood vessels, and serve as another example of a hypertension medication. Additional medications are sometimes used in treatment of hypertension and are therefore relevant examples in this context, such as, for example, alpha blockers, alpha-beta blockers, beta blockers, aldosterone antagonists, renin inhibitors, vasodilators, and central-acting agents.

The presently-disclosed subject matter also includes a device for use in identifying risk of cerebral vasospasm in a subject. The device can be, for example, a microfluidic device or an array of DNA oligonucleotides.

In some embodiments, the device includes a combination of probes, including a probe specific for each of at least one, two, three, four, five, six, seven, eight, nine, or ten miRNAs selected from the group consisting of: let-7b-5p, miR-9-3p, miR-15b-5p, miR-17-5p, miR-19b-3p, miR-20a-5p, miR-24-3p, miR-29a-3p, miR-125b-5p, and miR-142-3p.

In some embodiments, the device further includes one or more probes selected from the group consisting of miR-145, ath-miR-159a, miR-183, miR-200a, miR-302c-5p, miR-365, miR-502, miR-542-3p, miR-662, and miR-720. In some embodiments, the device further includes one or more probes selected from the group consisting of: let-7a, let-7b, let-7c, miR-103, miR-107, miR-124a, miR-1197, miR-125b, miR-1274b, miR-1298, miR-132, miR-142-3p, miR-142-5p, miR-143, miR-146a, miR-146b, miR-150, miR-155, miR-15a, miR-15b, miR-16, miR-17, miR-181a, miR-181c, miR-195, miR-19b, miR-204, miR-20a, miR-21, miR-210-3p, miR-221, miR-223, miR-23a, miR-23b, miR-24, miR-26a, miR-27a, miR-27b, miR-29a, miR-29b, miR-29c, miR-34a, miR-34b, miR-451, miR-484, miR-486-5p, miR-497, miR-520h, miR-553, miR-566, miR-643, miR-874, miR-9-3p, miR-9-5p, miR-92, Cel-miR-39-3p, and U6 snRNA.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

In certain instances, microRNAs (miRNAs) disclosed herein are identified with reference to names assigned by the miRBase Registry (available at www.mirbase.org). The sequences and other information regarding the identified miRNAs as set forth in the miRBase Registry are expressly incorporated by reference as are equivalent and related miRNAs present in the miRBase Registry or other public databases. Also expressly incorporated herein by reference are all annotations present in the miRBase Registry associated with the miRNAs disclosed herein. Unless otherwise indicated or apparent, the references to the Sanger miRBase Registry are references to the most recent version of the database as of the filing date of this Application.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

EXAMPLES

Example 1: Patient Cohorts

Following institutional review board (IRB) approval (#55914), all patients admitted to the University of Kentucky Chandler Medical Center (UKCMC) were screened for inclusion and exclusion criteria for this prospective, observational study. All patients greater than 18 years of age were included in this study if they had radiographically proven aSAH, a Modified Fischer Score >3 [38], and a ventriculostomy (EVD: external ventricular drain) was placed prior to post-bleed-day 3 (PBD3). Patients were excluded from this study if they arrived at the hospital in a non-survivable condition or were likely to die prior to PBD14 as determined by the attending neurosurgeon or neurointensivist. Patients were also excluded if they had a history of systemic inflammatory disease of any kind or were chronically dosed with a biologic inflammatory modulator. Finally, patients were also excluded if a legally authorized representative (LAR) could not be located by PBD3 or who refused (or their LAR refused) consent. Data from patients who were enrolled but died prior to PBD14 were not analyzed as the true extent of their potential CVS and delayed cerebral ischemia (DCI) may not have been discovered prior to their deaths.

During hospitalization, all patients were treated according to local standard of care, including early (within 48 hours of initial hemorrhage) diagnostic angiogram and endovascular coil or surgical clip obliteration of aneurysm, blood pressure control with intravenous and oral agents, scheduled nimodipine therapy, daily transcranial Doppler (TCD) analysis, sodium monitoring and replacement, and fluid balance monitoring to maintain euvolemia. Patients were considered to have CVS if, during their hospitalization, the TCD measurement demonstrated a mean flow velocity>120 cm/sec in either middle cerebral artery (MCA) and a calculated Lindegaard ratio>3.0 [39]. Patients with CVS and new neurologic abnormalities were treated with therapeutic hypertension and underwent digital subtraction angiography (DSA) and intra-arterial injection of verapamil. Patients with CVS and no new neurologic abnormalities underwent Computed Tomography Angiography (CTA) to evaluate and, if large-vessel vasospasm was identified, underwent DSA and intra-arterial injection of verapamil. Patients with CVS but without large-vessel vasospasm on CTA were treated with therapeutic hypertension and monitored for future changes in neurologic changes. Data on the development of CVS and other clinical outcomes were obtained from the patient, their family and their electronic medical record (EMR) at PBD30.

Example 2: Cell-Free CSF and Plasma Sample Collection

After written documentation from the patient or their legally authorized representative, baseline demographic data was obtained from the patient, their family and the EMR. CSF and plasma were collected by study personnel using a standard protocol at PBD 0, 1, 2, 3, 5, 7 and 10. Of note, CSF was collected directly from the patient using a sampling port inserted in the EVD drainage tubing at the time of placement. After samples were obtained, they were centrifuged at 3000×g for 5 minutes, the supernatant was then aliquoted into 250 microliter (µl) aliquots and frozen in a −80 C freezer until further analysis. The miRNA analysis was performed only from the specimens collected at PBD3 and PBD7, except in Example 18, in which analysis was performed from the specimens collected at PBD0, PBD1, PBD2, PBD3, PBD5, PBD7, and PBD10.

In addition, several cases were gifted from a deidentified data set, along with frozen plasma and CSF samples, from the University of Pennsylvania (UPENN). This data set and biofluids had already been collected and no information on data collection or sample preparation were available. For this reason, they were used in testing prediction model only.

As reference to control for basal levels of miRNA expression, CSF and plasma specimens from 8 healthy persons who had no clinically manifest neurological disease or diagnosis were procured from the University of Kentucky Alzheimer's Disease Center (UK-ADC) biobank.

Example 3: Experimental Design

A total of 39 patients and controls were analyzed in 3 temporally-separated groups according to the availability of the specimens at the time of analysis. Group A was analyzed first and included 18 aSAH patients (10 CVS−, 8 CVS+) from UKCMC and 8 healthy controls (HCs) from UK-ADC biobank. Group B was analyzed in next and included 9 aSAH patients including 2 experimental duplicates from Group A, 3 additional cases from UKCMC, and 4 cases gifted from UPENN. Finally, Group C was analyzed and included 6 aSAH patients from UKCMC. The data from Group A was used as a training set to build a risk prediction model for testing the discrimination ability of the miRNA panel in the subsequent 2 testing groups. The differences in demographics and clinical observations between CVS+ and CVS− groups were evaluated using Fisher's exact test.

A blinding procedure of sample analysis was implemented in this project. The physicians and persons who diagnosed and treated the patient, and those that collected and aliquoted the specimens did not perform the miRNA analysis. Likewise, miRNA analyses were performed by personnel blinded to patient data and clinical outcome.

Clinical and laboratory data were only unblinded after all data were acquired. The statisticians who constructed the prediction models were not involved in either the sample collection or miRNA analysis steps.

Example 4: Design of a Customized Brain and Vasculature Injury Related miRNA Panel A customized panel containing selected miRNAs that are associated with brain and vasculature injury was designed as described in a prior publication [40] and in the Results section. The selected miRNAs were then made into a customized TaqMan® miRNA RT-qPCR low density array (TLDA, Thermofisher, Waltham, MA USA) in 8×48 format that can simultaneously analyze 48 miRNAs in 8 independent samples.

Example 5: RNA Isolation from CSF and Plasma

CSF and plasma total RNA were isolated using miRNeasy Serum/Plasma Advanced Kit (Cat #: 217204, Qiagen, Hilden, Germany) following manufacturer's protocol. Briefly, aliquoted CSF or plasma specimens were thawed on ice and centrifuged at 3000×g for 5 minutes at 4 C to eliminate any potential aggregates while frozen. A 200 µl supernatant was transferred to a fresh tube. All the following steps are performed at room temperature and the centrifuge speed is carried out at 12,000×g. Sixty (60) µl of Buffer RPL was added to the supernatant and vortexed for 5 seconds, then incubated for 3 minutes; following a short spin, 1 µg of bacteriophage MS2 RNA (Cat #: 10165948001, carrier, Roche, Basel, Switzerland) and $5.6 \times 10^8$ copies of Cel-miR-39-3p (Cat #: 219610, spike-in RNA, QIAGEN, Hilden, Germany) were added to the mixture. The addition of synthetic cel-miR-39 served as an exogenous control for the RNA isolation step. Next, Buffer RPP (20 µl) was added, vortexed for 20 seconds, incubated for 3 minutes, and centrifuged for 3 minutes. The clear supernatant (~230 µl) was then transferred to a fresh tube with addition of 230 µl of isopropanol and mixed. The entire sample was then transferred to a MinElute column and RNA filter binding, washing, and drying steps were carried out as described in the manual, and RNA was eluted with 30 µl of nuclease-free water containing 0.5 U/µl RNAsin (RNase inhibitor, Cat #: N2115, Promega, Madison, WI, USA). Typically, extracellular biofluids contain very low quantity of RNA, often below the detection limit of spectrophotometers [41], therefore concentrations of isolated CSF or plasma RNA were not measured. In addition, because no prominent rRNA is expected in these cell-free specimens, RNA integrity number is irrelevant and was not determined.

Example 6: RT-qPCR Using Customized TaqMan® Low-Density Array (TLDA)

MiRNA reverse transcription and real time PCR detection procedures were performed following the manufacturer's instruction and are also described in detail in prior publications [42, 40]. Briefly, 3 µl of total RNA or nucleic acid free water (no template control) was reverse transcribed using the TaqMan® MicroRNA Reverse Transcription Kit (Cat #: 4366596, Thermofisher, Waltham, MA, USA) with custom-pooled specific RT primers. The resulting cDNA was preamplified with corresponding custom-pooled preamplification primers using TaqMan® PreAmp Master Mix (Cat #: 4391128, Thermofisher, Waltham, MA, USA). Each of the preamplified products was then mixed with TaqMan® Universal PCR Master Mix (Cat #: 4440040, Thermofisher, Waltham, MA, USA), transferred to individual TLDA sample ports and loaded to each well by spinning the cards in a centrifuge according to the manufacturer's instructions. Real-time quantitative PCR was carried out on ViiA™ 7 Real-Time PCR System (Thermofisher, Waltham, MA, USA) using the manufacturer's standard program (hold 2 minutes at 50° C., followed by 10 minutes at 95° C., then 40 cycles of 15 seconds at 95° C. and 1 minute at 60° C.).

Example 7: TLDA Data Processing

Raw quantitative real-time PCR run files were imported to the ThermoFisher Data Cloud and further analyzed using ThermoFisher Cloud Software—Relative Quantification. The relative threshold cycle (Crt) method [43] was applied to acquire the quantitative Crt values from all TLDA runs in each experiment. The Crt method uses an algorithm that sets a threshold for each individual amplification curve thus reducing variation across the replicates while maintaining the same dynamic range. Crt values that failed software-defined QC and values equal to or more than 35 were considered as undetectable and excluded from further analysis. Furthermore, a miRNA would be removed from analysis when it was not detected in one third of tested samples. Initially, 2 miRNAs, miR-1274b and miR-204, were selected as potential normalizers for CSF miRNA expression. However, the first patient cohort study showed that these two miRNAs had significantly different values between various groups and thus could not be used as endogenous controls. Moreover, since the TLDA consisted of specific selected miRNAs, the additional internal normalizer could not be identified. Therefore, the Global Mean Normalization method [44] was then used to normalize the TLDA data. Raw Crt values were exported and the geometric mean of a given sample was used to obtained ΔCrt values calculated as ΔCrt=Crt-taget−Crt-geomean for each miRNA. The time for processing 2-8 samples from RNA isolation, TaqMan TLDA assay to data analysis is around 6-8 hrs, including, for CSF/plasma (200 µL): (a) RNA isolation (30 min), (b) Reverse transcription (135 min), (c) Pre-amplification (75 min), (d) TaqMan miRNA TLDA (110 min), and (e) data analysis (15 min).

Example 8: Statistical Analysis

GraphPad Prism 8.0.2. (San Diego, CA, USA) and R (version 4.0.2) [45] were used for statistical analysis. Student's t-tests (2-tailed) were used to evaluate mean differences for individual miRNAs between the control and aSAH patient groups, or CVS+ and CVS-patient groups. A 95% confidence interval was used in all data analyses with p<0.05 being considered statistically significant. The receiver operating characteristics (ROC) were generated to evaluate CVS discrimination ability for the best performing individual miRNAs.

Example 9: Construction of CVS Prediction Model

Figure 4:
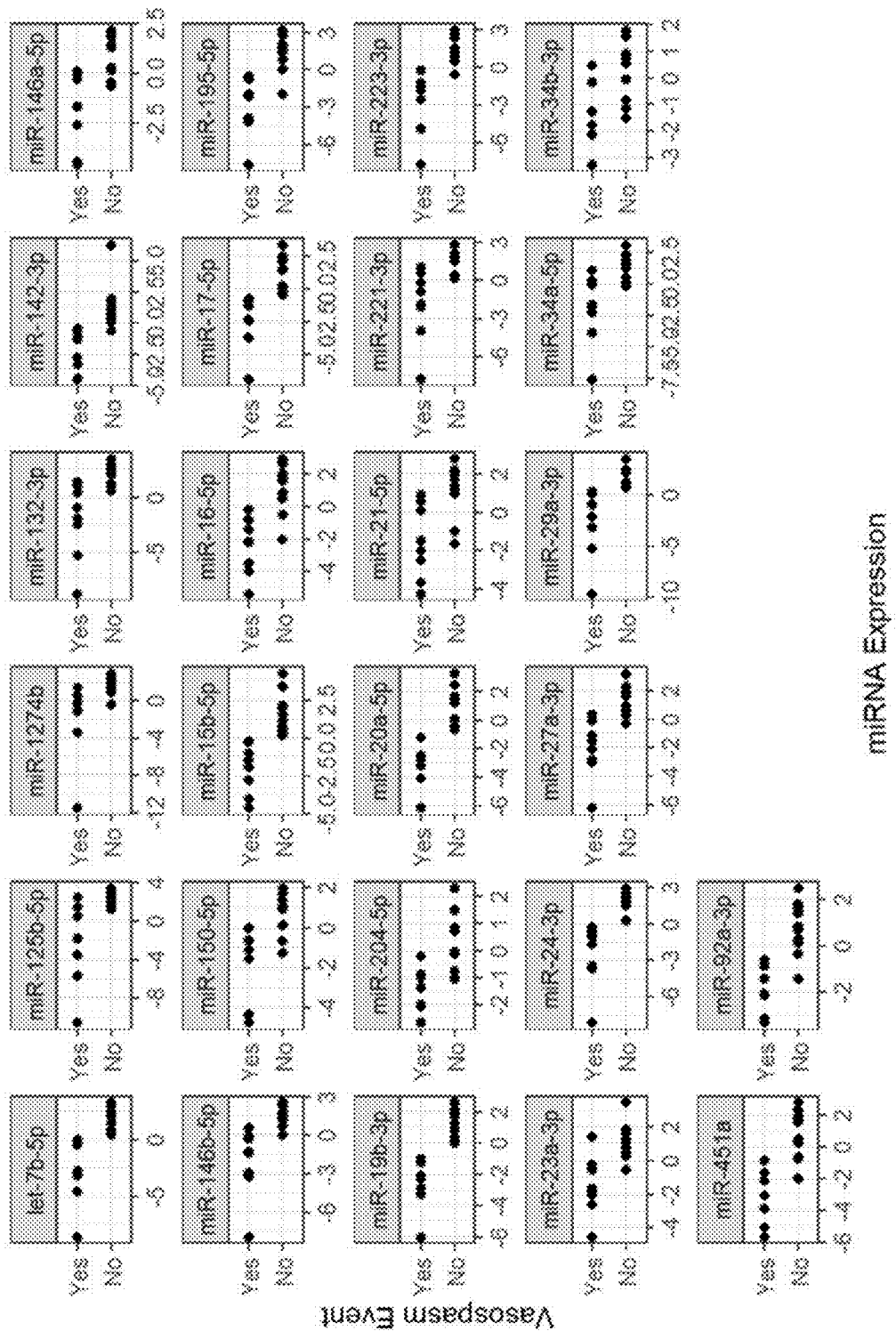

A model to predict CVS events was constructed using the GroupA CSF-PBD3 dataset (18 patients: 10 CVS−, 8 CVS+). The model building process used the 26 miRNAs ('variables') in the panel that did not have any missing data across all 3 analysis aSAH patient groups (GroupA, GroupB, and GroupC). Among the 26 miRNAs, the expression levels of 7 miRNAs exhibited perfect discrimination between CVS+ and CVS− patient groups in the GroupA dataset (i.e., CVS+ patient measurements were either all greater or all less than those from CVS− patients; FIG. 4). These 7 miRNAs each served as individual predictor in a consensus predictive tool. The midpoint of the maximum or minimum value from the CVS+ patients and the midpoint of the minimum or maximum value from the CVS− patients was used as the cutoff value in the prediction, depending on which direction confers risk. The remaining 19 miRNAs without missing data and that did not demonstrate perfect discrimination were used to generate a decision tree using the Rpart (Recursive partitioning and regression trees) algorithm in R [46]. The model specifications were: 1) minimum number of observations for a split to be attempted (1 observation); 2) cost-complexity parameter (CP=0.01); 3) specification of priors (proportional to data counts); and 4) splitting measure used was the Gini Index. Model performance was evaluated based on overall error rate through a confusion matrix.

Example 10: Demographic and Pathological Data of Study Cohorts

Seventy-seven (77) patients were admitted to UKCMC with aSAH over a defined period, of these, 27 were included in this study (see baseline patient demographics in Table 1). Of the 50 patients who were excluded, 34 did not have an EVD placed, 8 were not expected to survive, 4 patients did not have an available LAR present within first 72 hours, 2 patients or their LAR refused consent, and 2 patients had pre-existing systemic inflammatory diseases. Clinical data and biospecimen samples from all 27 patients included in the study were analyzed. There were no significant differences between the patients with CVS (CVS+) and patients without CVS (CVS−) based on the distribution of age, gender, height, weight, body mass index, ethnic origin. Furthermore, no significant differences were observed between the two study groups in the classification of the severity of subarachnoid hemorrhage (Hunt Hess score, WFNS score, and modified Fischer score), location of the aneurysm, or the type of aneurysm obliteration. The average age of the HC group was older than that of aSAH patients, however the primary interest was in the comparison between CVS+ and CVS− patients and the HC group served as a secondary reference. Therefore, the age difference was not considered a confounding factor.

TABLE 1

Demographic and descriptive statistics of the study population. Baseline demographics of aneurysmal subarachnoid hemorrhage (aSAH) patients grouped based on whether or not they developed vasospasm during hospitalization. Continuous variables are described as mean ± SD with differences evaluated by the unpaired t-test. Categorical variables are described as N and % with differences evaluated by Fisher's exact test.

|  | Healthy Control N = 8 | CVS N = 12 | No CVS N = 17 | p-value (CVS vs. No CVS) |
|---|---|---|---|---|
| Age (years) | 74.3 ± 7.0 | 59.3 ± 18.2 | 59.5 ± 12.3 | 0.99 |
| Gender (male) | 3 (37.5%) | 3 (25.0%) | 9 (52.9%) | 0.25 |
| Height (cm) | N.D. | 166.9 ± 11.6 | 171.8 ± 10.1 | 0.24 |
| Weight (kg) | N.D. | 97.1 ± 27.4 | 92.7 ± 26.8 | 0.67 |
| Body Mass Index (kg/m$^2$) | N.D. | 34.6 ± 7.7 | 30.9 ± 6.6 | 0.18 |
| Ethnic Origin (White/Caucasian) | 8 (100%) | 11 (1.7%) | 15 (88.2%) | 1.00 |
| Hunt Hess Score (3-5) | N/A | 8 (66.7%) | 10 (58.8%) | 0.72 |
| WFNS Score (3-5) | N/A | 6 (50.0%) | 5 (29.4%) | 0.44 |
| Modified Fischer Score (4) | N/A | 6 (50.0%) | 7 (41.1%) | 0.71 |
| Aneurysm Located (yes) | N/A | 12 (100%) | 13 (76.5%) | 0.12 |
| Aneurysm Location (anterior) | N/A | 7 (58.3%) | 7 (53.9%) | 0.46 |
| Aneurysm Obliteration Type (coiled) | N/A | 11 (91.7%) | 13 (100%) | 0.37 |

N.D.: no data available;
N/A: N/A = not applicable
Baseline demographics of aneurysmal subarachnoid hemorrhage (aSAH) patients from UKCMC grouped based on whether or not they developed cerebral vasospasm (CVS) during hospitalization. Continuous variables are described as mean ± SD with differences evaluated by an unpaired t-test. Categorical variables are described as N and % with differences evaluated by Fisher's exact test. N.D.: no data available; N/A: not applicable.

Example 11: Design and Performance of the Customized Brain and Vasculature Injury Related miRNA Panel A customized miRNA panel was developed, consisting of 47 miRNAs relevant to brain and vasculature injury events (Table 2) to quantify miRNA expression levels in samples from aSAH patients and HCs. MiRNAs that met any of following criteria were selected for inclusion in the panel: 1) strong association with CNS injury or cerebrovascular damage, either identified in prior studies [22, 40] or reported in the literature; 2) implication in previous biomarker studies related to CNS injury (TBI, SCI, or neurodegeneration) or stroke; 3) potential data normalizer, control for contamination, and control for isolation procedure; 4) is detectable in CSF and plasma. The panel contained one additional rodent specific miRNA and the manufacturer's mandatory control U6, both of which were excluded from analysis. CSF and plasma miRNA from a total of 31 aSAH patients (27 patients from UKCMC and 4 from UPENN) and 8 HCs were included in the TLDA analysis.

TABLE 2

Selection of brain and vasculature injury related miRNAs.

| miRNA[1] | Relevance to aSAH and cerebral vasculature |
|---|---|
| hsa-let-7a-5p[2] | Inflammatory/immune response |
| hsa-let-7b-5p[2] | Angiogenesis/inflammatory & immune response |
| hsa-let-7c-5p[2] | Inflammatory/immune response |

TABLE 2-continued

Selection of brain and vasculature injury related miRNAs.

| miRNA[1] | Relevance to aSAH and cerebral vasculature |
|---|---|
| hsa-miR-103a-3p[2] | Cell migration/wound healing |
| hsa-miR-107[2] | Inflammatory response/cell migration/wound healing |
| hsa-miR-125b-5p[2] | Cell proliferation/neuronal integrity |
| hsa-miR-1274b[3] | Potential normalizer (CSF) |
| hsa-miR-1298-5p[2] | Neural regeneration |
| hsa-miR-132-3p[2] | Vascular angiogenesis |
| hsa-miR-142-3p[2] | Inflammatory & immune response |
| hsa-miR-142-5p | Inflammatory & immune response |
| hsa-miR-144-3p | Proliferation/apoptosis/oxidative stress |
| hsa-miR-146a-5p[2] | Inflammatory/immune response |
| hsa-miR-145b-5p | Inflammatory/immune response |
| hsa-miR-150-5p | Inflammatory/immune response/BBB permeability |
| hsa-miR-153-3p[2] | Neurogenesis |
| hsa-miR-155-5p[2] | Inflammatory/immune response/arteriogenesis |
| hsa-miR-15a-5p[2] | Vascular angiogenesis |
| hsa-miR-15b-5p[2] | Apoptosis/inflammatory response |
| hsa-miR-16-5p[2] | Vascular angiogenesis |
| hsa-miR-17-5p[2] | Neovascularization/apoptosis/proliferation |
| hsa-miR-181a-5p[2] | Apoptosis/inflammatory response |
| hsa-miR-181c-5p[2] | Apoptosis/inflammatory response |
| hsa-miR-195-5p[2] | Homeostasis of vessel smooth muscle cells |
| hsa-miR-19b-3p[2] | Neovascularization/apoptosis/proliferation |
| hsa-miR-204-5p[2,3] | Apoptosis/proliferation |
| hsa-miR-20a-5p[2] | Neovascularization/apoptosis/proliferation |
| hsa-miR-21-5p[2] | Apoptosis/inflammatory |
| hsa-miR-221-3p[2] | Apoptosis/inflammatory |
| hsa-miR-223-3p[2] | Inflammatory/immune response |
| hsa-miR-23a-3p | Mitochondrial function/apoptosis |
| hsa-miR-23b-3p[2] | Mitochondrial function/apoptosis |
| hsa-miR-24-3p[2] | Apoptosis/proliferation |
| hsa-miR-27a-3p[2] | Autophagy/apoptosis |
| hsa-miR-27b-3p[2] | Autophagy/apoptosis |
| hsa-miR-29a-3p[2] | Apoptosis/proliferation/immune response |
| hsa-miR-29b-3p[2] | Apoptosis/proliferation/immune response |
| hsa-miR-29c-3p[2] | Apoptosis/proliferation/immune response |
| hsa-miR-34a-5p[2] | Autophagy/inflammatory response |
| hsa-miR-34b-3p[2] | Autophagy/inflammatory response |
| hsa-miR-497-5p | Apoptosis/inflammatory response |
| hsa-miR-874-3p | Apoptosis/inflammatory response |
| hsa-miR-9-5p[2] | Neurogenesis & differentiation |
| hsa-miR-92a-3p[2] | Neovascularization/apoptosis/proliferation |
| hsa-miR-124-3p[2] | Neurogenesis & differentiation & inflammatory response |
| hsa-miR-155-5p[4] | |
| hsa-miR-451a[2] | Apoptosis/inflammatory response/RBC enriched |

Note:
[1]All selected miRNAs are known to be associated with CNS injuries or cerebral vasculature damage;
[2]miRNA has been implicated in biomarker studies related to CNS (TBI or SCI) or stroke;
[3]miRNA is a potential normalizer for CSF;
[4]mmu-miR-155-5p was included for a separate unrelated rodent study.

Figure 1F:
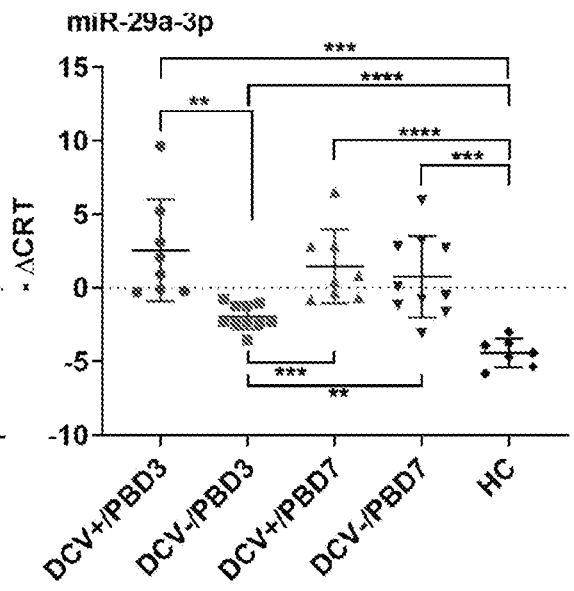
Figure 2A:
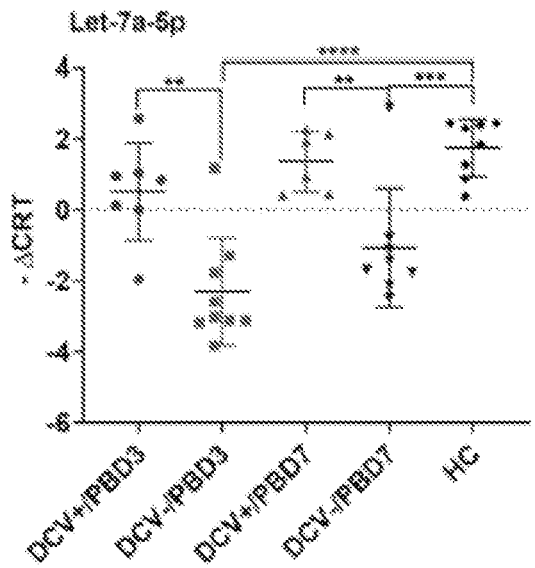
FIGS. 2A-2F. Individual plasma miRNAs that showed highly differential expression in CVS+, CVS−, and HC groups. The differential miRNA expression levels are expressed as −$\Delta$CRT and a two tailed Student's t-test was used to evaluate the difference between groups. Significant levels expressed as: **: $p<0.0001$; *: $p=0.0001$ to 0.001; **: $p=0.001$ to 0.01; *: $p=0.01$ to 0.05
Figure 2B:
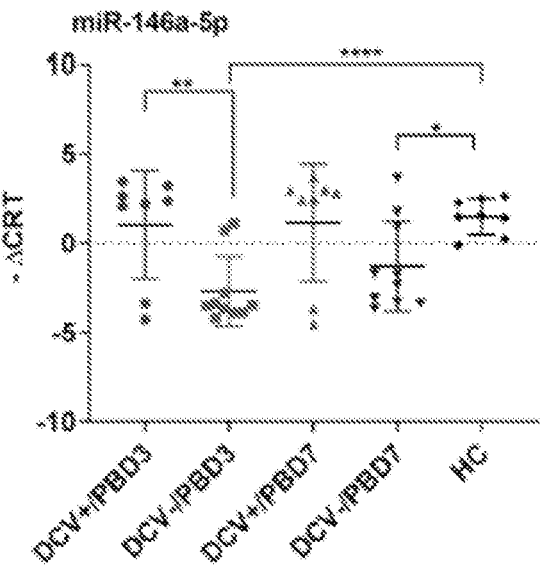
Figure 2C:
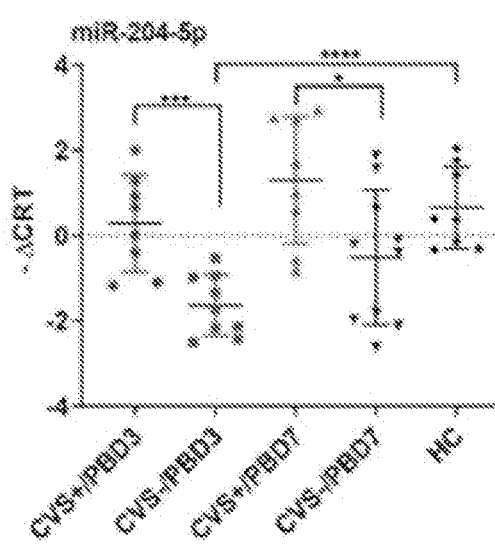
Figure 2D:
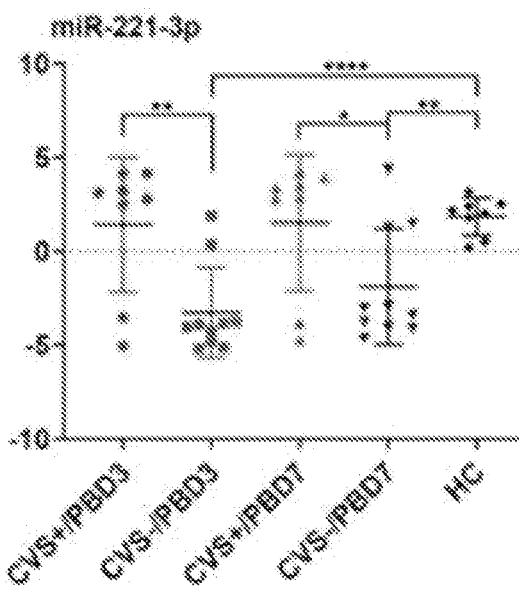
Figure 2E:
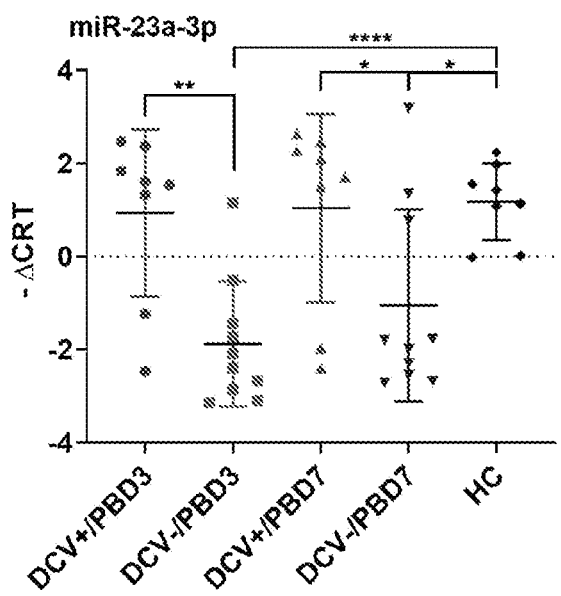
Figure 2F:
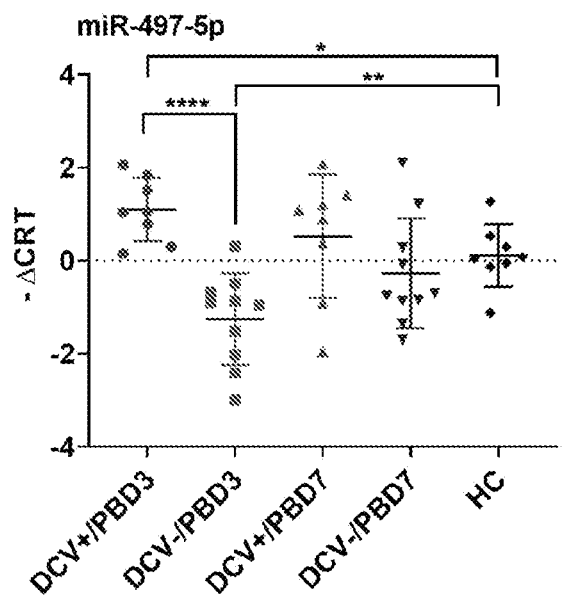

Data presented in FIGS. 1-3 and Table 3 represent the analysis and results using Group A dataset. Overall, the designed panel detected most of the selected miRNAs. A miRNA was deemed to be detectable based on whether it exhibited a Crt<35 in at least two-thirds of total specimens. Based on these criteria, 6 miRNAs from the CSF samples (miR-107, miR-144-3p, miR-153-3p, miR-15a-5p, miR-29b-3p, and miR-874-3p) and 6 miRNAs from the plasma samples (miR-124-3p, miR-144-3p, miR-1298-5p, miR-153-3p, miR-874-3p, and miR-9-5p) were removed from further analysis. Overall, a clear and distinct miRNA expression pattern was observed between the CVS+ and CVS− patient groups, aSAH patient groups and HCs, as well as between sampling times (PBD3 vs PBD7) in both CSF and plasma samples (Heatmap data not shown).

TABLE 3

Significant differential expression levels of brain and vasculature injury related miRNAs

| | CSF | | | | | | Plasma | | | | | |
|---|---|---|---|---|---|---|---|---|---|---|---|---|
| miRNA | I | II | III | IV | V | VI | I | II | III | IV | V | VI |
| let-7a-5p | ** | ns | * | ns | ns | ns | ** | ** | ns | **** | ns | *** |
| let-7b-5p | *** | ns | **** | *** | **** | *** | ns | ns | ns | * | ns | ns |
| let-7c-5p | ** | ns | ** | ns | * | * | ns | ns | ns | * | ns | ns |
| miR-103a-3p | * | ns | UD in heathy controls | | | | ns | ns | ns | **** | ns | ** |
| miR-107 | | | UD | | | | *** | * | *** | ns | ns | * |
| miR-125b-5p | ** | ns | ** | ns | ** | ** | ns | ns | ns | ns | ns | ns |
| miR-1274b | * | ns | * | ns | ** | ** | ** | ns | ** | ns | ** | ns |
| miR-1298-5p | ns | ns | ns | ns | ** | ns | | | UD | | | |
| miR-132-3p | ** | ns | ** | ** | *** | ** | * | ns | ns | ** | ns | ns |
| miR-142-3p | *** | ns | **** | *** | *** | **** | ** | * | ns | *** | ns | * |
| miR-142-5p | *** | ns | UD in heathy controls | | | | * | ns | ns | ** | ns | ns |
| miR-144-3p | | | UD | | | | | | UD | | | |
| miR-145a-5p | *** | ns | **** | *** | **** | *** | ** | ns | ns | **** | ns | * |
| miR-146b-5p | ** | ns | *** | *** | *** | *** | * | ns | ns | **** | ns | ** |
| miR-150-5p | ** | ns | **** | ** | * | * | ns | ns | ns | ** | ns | ns |
| miR-153-3p | | | UD | | | | | | UD | | | |
| miR-155-5p | ns | ns | ns | ns | ns | ns | ** | * | ns | **** | ns | *** |
| miR-15a-5p | | | UD | | | | ** | ns | ns | ** | ns | * |
| miR-15b-5p | **** | ns | *** | * | ** | * | * | ns | ns | *** | ns | ** |
| miR-16-5p | *** | ns | **** | *** | ** | ** | ns | ns | ns | ns | ns | ns |
| miR-17-5p | *** | ns | **** | *** | ** | ** | * | ns | ns | * | ns | ns |
| miR-181a-5p | *** | ns | * | ns | * | ns | ** | ns | ns | *** | ns | ** |
| miR-181c-5p | ns | ns | ns | ns | ns | ns | ** | ns | ns | *** | ns | * |
| miR-195-5p | *** | ns | **** | ** | *** | ** | ns | ns | ns | ns | ns | ns |
| miR-19b-3p | **** | ns | **** | **** | **** | **** | * | ns | ns | ns | ns | ns |
| miR-204-5p | ** | ns | **** | * | * | ns | *** | * | ns | **** | ns | ns |
| miR-20a-5p | **** | ns | **** | *** | **** | *** | * | ns | ns | * | ns | ns |

TABLE 3-continued

Significant differential expression levels of brain and vasculature injury related miRNAs

| miRNA | CSF | | | | | | Plasma | | | | | |
|---|---|---|---|---|---|---|---|---|---|---|---|---|
| | I | II | III | IV | V | VI | I | II | III | IV | V | VI |
| miR-21-5p | ** | ns | **** | **** | **** | **** | ** | ns | ns | * | ns | ns |
| miR-221-3p | ** | ns | ** | * | *** | *** | ** | * | ns | **** | ns | ** |
| miR-223-3p | *** | ns | **** | **** | **** | **** | ** | ns | ns | **** | ns | ns |
| miR-23a-3p | ** | ns | *** | ** | *** | *** | ** | * | ns | **** | ns | * |
| miR-23b-3p | * | ns | ns | ns | ns | ns | ** | * | ns | *** | ns | * |
| miR-24-3p | *** | ns | **** | *** | *** | *** | ** | ns | ns | *** | ns | * |
| miR-27a-3p | *** | ns | **** | * | ** | **** | ** | ns | ns | *** | ns | * |
| miR-27b-3p | *** | ns | ** | ns | ns | * | * | ns | ns | *** | ns | * |
| miR-29a-3p | ** | ns | *** | **** | **** | *** | ** | ns | ns | ** | ns | ns |
| miR-29b-3p | | | UD | | | | * | ns | ns | ns | ns | ns |
| miR-29c-3p | ** | ns | ** | * | *** | ** | * | ns | ns | ns | ns | ns |
| miR-34a-5p | ** | ns | *** | *** | **** | **** | * | ns | * | ns | * | * |
| miR-34b-3p | ** | ns | *** | ns | ns | ns | ns | ns | ** | ns | ** | ns |
| miR-497-5p | *** | ns | ** | ns | ** | ** | **** | ns | * | ** | ns | ns |
| miR-874-3p | | | UD | | | | | | | UD | | |
| miR-9-5p | * | ns | ns | ns | ns | ns | | | | UD | | |
| miR-92a-3p | *** | ns | **** | **** | **** | **** | | ns | ns | ns | ns | ns |
| nsmiR-124-3p | ** | ns | ** | * | ** | * | | | | UD | | |
| miR-451a | *** | ns | * | ns | ns | ns | ns | ns | ns | ns | ns | ns |

Note:
Custom brain and vasculature injury miRNA panel TLDA was used to analyze CSF and plasma specimens from GroupA patients (8x CVS+, 10x CVS−, 8x HC). The differential expression was evaluated using Student's t-test (2-tailed) between I: CVS+ vs. CVS−, PBD3; II: CVS+ vs CVS−, PBD7; III: CVS+ vs HC, PBD3; IV: CVS− vs. HC, PBD3; V: CVS+ vs HC, PBD7; VI: CVS− vs HC, PBD7. Asterisk symbols for significant levels.
****: p < 0.0001;
***: p = 0.0001 to 0.001;
**: p = 0.001 to 0.01;
*: p = 0.01 to 0.05;
ns: p = 0.05.
UD: undetectable

Example 12: Individual miRNA Performance in CSF and Plasma

The majority of the selected miRNAs in CSF and plasma showed significant differential expression between CVS+ and CVS− at the early sampling time point of PBD3 (Table 3). At PBD7, the differential expression between CVS+ and CVS− was reduced (Table 3). The differential patterns were especially robust when using the panel to analyze CSF specimens obtained at PBD3. Specifically, 37 miRNAs from the CSF demonstrated highly significant differences in samples collected from CVS+ relative to CVS− patients at PBD3. Several miRNAs including Let-7b-5p, miR-15b-5p, miR-17-5p, miR-19b-3p, miR-20a-5p, miR-24-3p, and miR-29a-3p exhibited remarkable differential expression between the CVS+ and CVS− groups at PBD3, as well as between the CVS+/PBD3 group and HCs (FIGS. 1A-1F, FIG. 4). With respect to the plasma specimens, 29 miRNAs demonstrated significant differential expression between the CVS+ and CVS-groups at PBD3 (Table 3). There also were several individual plasma miRNAs (Let-7a-5p, miR-146a-5p, miR-204-5p, miR-221-3p, miR-23a-3p, miR-497-5p) that showed high differential expression patterns between the CVS+ and CVS− groups at PBD3 (FIGS. 2A-2F).

Figure 3A:
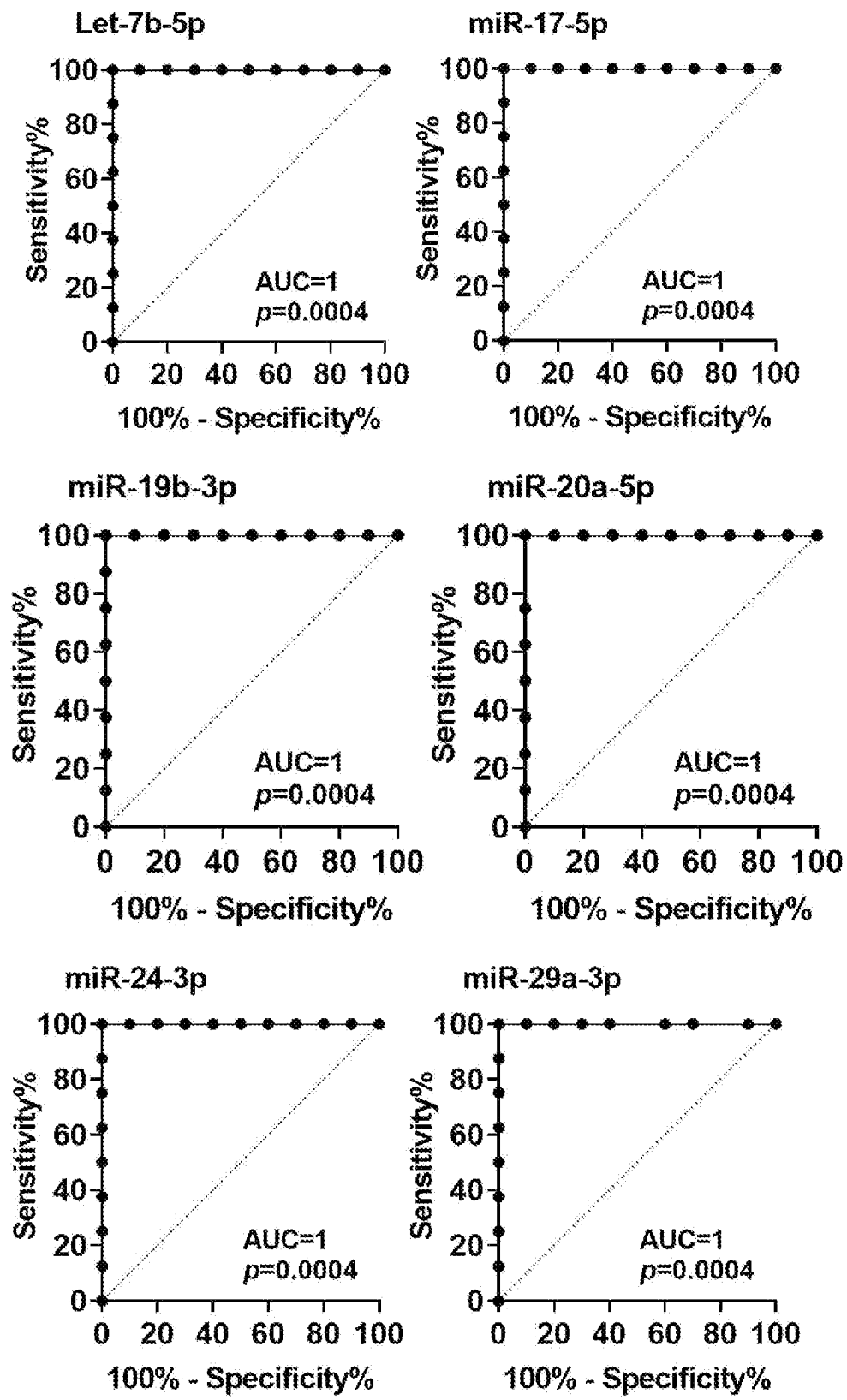
FIGS. 3A and 3B. ROC analysis of miRNAs using GroupA CSF and plasma data collected at PBD3 from aSAH patients. ROC curve constructed using a) CVS+ and CVS− groups of CSF miRNA data; b) CVS+ and CVS− groups of plasma miRNA data FIG. 4. Distribution of miRNA expression values for 26 miRNAs between CVS+ and CVS− of the GroupA cases. Each filled circle corresponds to a single case with "Yes" referring to CVS+ and "No" referring to CVS.
Figure 3B:
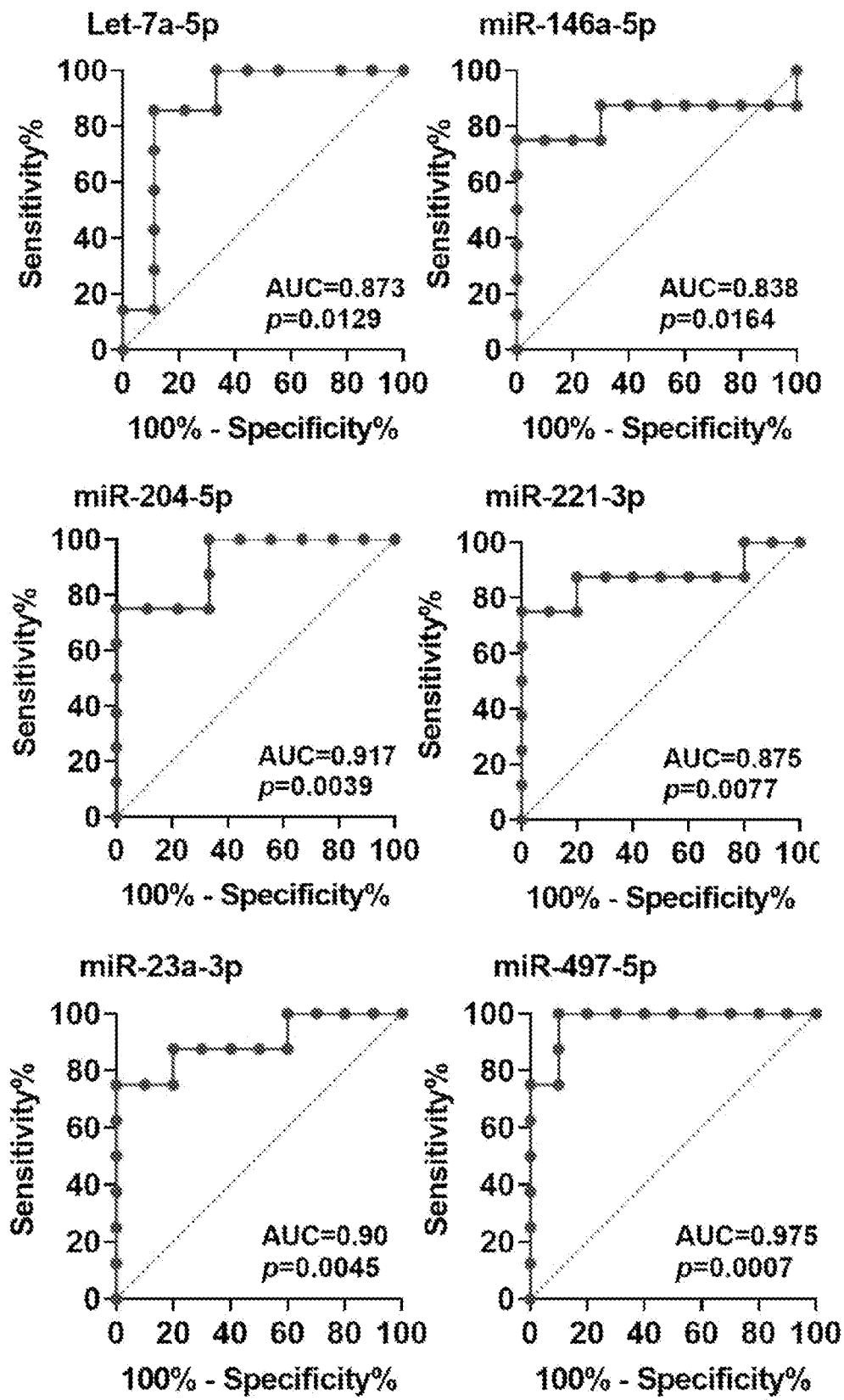

Example 13: Receiver Operating Characteristic (ROC) Curves of Individual miRNAs The sensitivity and specificity of individual miRNAs as predictors of CVS were examined using the area under the ROC curve (AUC). Many miRNAs demonstrated an AUC greater than 0.9 in CSF collected at PBD3, indicating a highly significant predictive ability of these miRNAs (FIG. 3A). Of note, the AUC of Let-7b-5p, miR-15b-5p, miR-17-5p, miR-19b-3p, miR-20a-5p, miR-24-3p, and miR-29a-3p reached 1 (AUC=1), signifying a perfect discrimination between CVS+ and CVS− patients at a time point prior to CVS onset. Similarly, several plasma miRNAs also achieved AUCs greater than 0.8 (FIG. 3B), demonstrating a robust ability of selected miRNA for discriminating CVS in two biofluid types.

Figure 5:
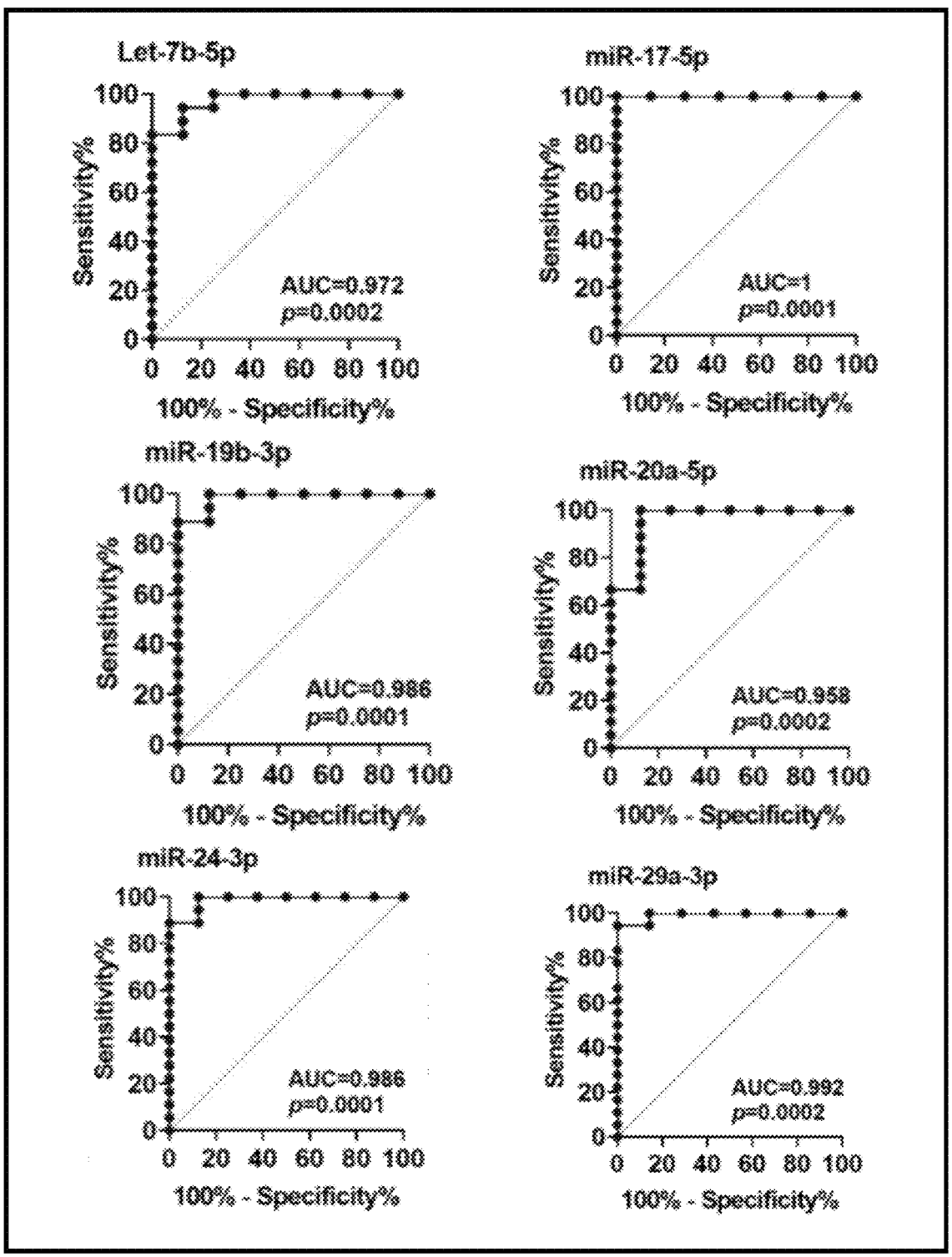
FIG. 5. ROC curves constructed using CSF miRNA data (PBD3) from aSAHs (CVS+ plus CVS− group) and HCs.

High AUC values were also achieved when comparing aSAH patients and HCs using CSF-PBD3 data (FIG. 5), indicating that selected CSF miRNAs can also discriminate aSAH patients from HCs.

Example 14: Prediction Accuracy of the Custom miRNA Panel on GroupB and GroupC The CSF-PBD3 data from GroupA (18 patients: 10 CVS− and 8 CVS+) was then used to build a predicting model, and the dataset from the remaining 15 cases from GroupB (including 2 replicates from GroupA) and GroupC was used for model testing and retrospective risk prediction. Using the CSF miRNAs with an AUC value of 1 as predictors a risk prediction accuracy of 93% was achieved with miR-19b-3p and miR-29a-3p using the corresponding cutoff values of −0.481 and 0.53, respectively (Table 4). In contrast, miR-24-3p achieved a 73% accuracy for the test dataset using the corresponding cutoff value of −0.015.

TABLE 4

Overall performance of CVS risk prediction of 7-miRNA panel. The table includes seven highly predictive individual miRNAs and the prediction using the decision tree. The cutoff values for each individual miRNA predictor were the mean of the values from the CVS+ and CVS− cases.

| Test Case | Let-7b-5p | miR-15b-5p | miR-17-5p | miR-19b-3p | miR-20a-5p | miR-24-3p | miR-29a-3p | Decision Tree | Vote | Observation |
|---|---|---|---|---|---|---|---|---|---|---|
| 1 | True Positive | True Positive | True Positive | True Positive | True Positive | False Negative | True Positive | True Positive | Yes | Yes |
| 2 | True Negative | True Negative | True Negative | True Negative | True Negative | True Negative | True Negative | True Negative | No | No |
| 3 | True Positive | True Positive | True Positive | True Positive | True Positive | True Positive | True Positive | True Positive | Yes | Yes |
| 4 | False Positive | False Positive | False Positive | False Positive | False Positive | False Positive | False Positive | False Positive | Yes | No |
| 5 | True Positive | True Positive | True Positive | True Positive | True Positive | True Positive | True Positive | True Positive | Yes | Yes |
| 6 | False Positive | True Negative | True Negative | True Negative | True Negative | True Negative | True Negative | True Negative | No | No |
| 7 | True Positive | True Positive | True Positive | True Positive | True Positive | False Negative | True Positive | True Positive | Yes | Yes |
| 8 | True Negative | True Negative | True Negative | True Negative | True Negative | True Negative | True Negative | True Negative | No | No |
| 9 | True Positive | True Positive | True Positive | True Positive | True Positive | True Positive | True Positive | True Positive | Yes | Yes |
| 10 | True Negative | True Negative | True Negative | True Negative | True Negative | False Positive | True Negative | True Negative | No | No |
| 11 | True Negative | True Negative | True Negative | True Negative | True Negative | True Negative | True Negative | True Negative | No | No |
| 12 | True Positive | True Positive | True Positive | True Positive | True Positive | False Negative | True Positive | True Positive | Yes | Yes |
| 13 | True Positive | True Positive | True Positive | True Positive | True Positive | False Negative | True Positive | True Positive | Yes | Yes |
| 14 | True Negative | False Positive | True Negative | True Negative | True Negative | False Positive | True Negative | True Negative | No | No |
| 15 | False Positive | False Positive | False Positive | True Negative | False Positive | True Negative | True Negative | False Positive | Yes | No |
| Cutoff | 0.248 | −0.038 | −0.603 | −0.481 | −0.925 | −0.011 | 0.530 | | | |
| Correct Predictions | 12 | 12 | 13 | 14 | 13 | 11 | 14 | 13 | 13 | |
| Accuracy | 0.80 | 0.80 | 0.87 | 0.93 | 0.87 | 0.73 | 0.93 | 0.87 | 0.87 | |

Example 15: Decision Tree (DT) Results

MiRNAs with an AUC less than 1 were used to generate a decision tree model. Out of the 19 miRNA variables entered into the model, miR-142-3p and miR-1274b were identified as key variables in the prediction process. This model correctly predicted 100% of the training dataset (Group A), and 87% of the test dataset (Group B+Group C, Table 4).

Example 16: Overall Prediction of 7-miRNA Panel

Table 4 presents a consensus prediction table incorporating 7 miRNAs with a perfect AUC of 1 and additional 19 miRNAs from the decision tree in the training data set. The outcome for each testing subject was predicted when at least 5 of the 8 criteria were met for either CVS+ or CVS−. The majority of the predictions were uniformly accurate across the test dataset with two exceptions out of 15 cases. Test case 4 had only false positive predictions across all eight predictors from the panel, while test case 15 resulted in 5 out of 8 false positive predictions. Despite the two false positive predictions, the overall performance of the custom panel in predicting CVS risk was 87% accurate.

Example 17: Observations Related to Examples 1-16

In the study described in these Examples, an effective miRNA panel was successfully developed and validated, which accurately predicts the risk of CVS in aSAH patients from CSF obtained 3 days after aneurysm rupture. It is believed that this is the first study utilizing a panel of selected brain and vasculature injury related miRNAs to develop a CVS biomarker panel using readily available patient biofluids. The data indicate that the panel possesses a remarkable ability in predicting CVS events in which the discrimination accuracy reaches 87%. Moreover, the procedure from sample collection to obtaining predictive data can be completed in as little as 6 hrs. The panel and the procedure described in the study can be further developed into an accurate, rapid, and cost-effective diagnosis tool in clinical practice for an active monitoring and timely treatment of CVS.

The potential of miRNAs serving as CVS or DCI biomarkers was recently explored in several reports [47-52, 34, 53, 54]. These studies confirmed that dysregulated miRNA expression is associated with aSAH, DCI, and CVS and that changes in miRNA expression could be observed in extracellular fluid. However, there is no consensus in the limited literature for targeting biofluid miRNAs as a valid biomarker for predicting DCI or CVS. This is due, in part, to significant variability across studies, including differences in sampling size (between 4 and 129 cases), type of biofluid used (whole blood, CSF, serum, plasma), collection time points (ranging from 1 to 14 days), as well as different methodologies for miRNA analysis. Importantly, several published methods utilized time-consuming and costly analytical methodologies such as next-generation sequencing and microarray [48, 49, 52] that, while informative, may limit or constrain clinical applications.

The major difference between the current study and other reports is that the current study resulted in the development of a miRNA panel with selected miRNAs that are highly relevant to brain and vasculature injury events rather than using individual miRNAs or profiling all miRNAs to assess the risk of CVS. This strategy directly targets a pathological condition by employing a dedicated set of miRNAs that are involved in CVS-related biological processes. By doing so, the likelihood of identifying responsive biomarkers is much greater, and may be achieved using a smaller patient cohort. Furthermore, multiple potential miRNA biomarkers can be used concomitantly in the overall assessment of CVS risk to ensure prediction accuracy.

Analysis of this unique panel revealed an overall differential expression pattern of selected miRNAs between aSAH patients and neurological HCs in both CSF and plasma, with the CSF samples showing the most pronounced difference. More importantly, the panel showed a remarkable ability to distinguish between aSAH patients with or without CVS. This was particularly evident in CSF samples from PBD3, a time point that is typically prior to the onset of CVS. In the independent cohort studies (GroupB and GroupC), the predictors generated from GroupA correctly predicted 11 (miR-24-3p, 73% accuracy) to 14 (miR-19b-3p and miR-29a-3p, 93% accuracy) out of a total of 15 cases with an overall prediction accuracy is as high as 87%. It is important to point out that all of the predictor miRNAs identified case 4 to be CVS positive when in fact it was CVS negative resulting in a false positive prediction. Likewise, five of the eight predictors incorrectly identified case 15 to be CVS positive, resulting in another false positive prediction. It is not entirely clear why these two cases resulted in incorrect predictions, and it may be related, in part, with the complex clinical conditions or comorbidities of the individuals.

An important advantage of the selected panel is that individual miRNAs are easily replaced if they do not perform well. For example, not all of the miRNAs on the current panel contributed to CVS prediction and several miRNAs were excluded from further analysis due to their low expression levels (e.g. miR-144-5p, miR-153-3p, and miR-874-3p). In addition, other miRNAs, such as miR-1298-5p in CSF and miR-16-5p in plasma, did not differentiate between CVS+ and CVS− patients. Therefore, replacing these miRNAs with other candidate miRNAs that may prove more effective in CVS prediction will be considered in future studies. For example, miR-516a-5p, miR-566, and miR-1197 were not included in the panel and appear to be differentially expressed in CSF samples of CVS+ and CVS− patients [51]. Other candidate miRNAs may include miR-502-5p and miR-1297 whose expression levels in serum were associated aSAH with severity and prognosis [55].

Several miRNAs in the panel were previously reported to be linked to CVS or DCI in aSAH patients. Significantly increased levels of miR-21-5p and miR-221-3p in CSF were shown to associate with DCI and miR-221-3p, miR-132-3p, and miR-19b-3p were associated with CVS [47]. In addition, CSF expression levels of miR-27a-3p, were reported to be differentially expressed between aSAH patients with or without CVS [51]. Finally, temporal changes in Let-7b-5p and miR-92a-3p in CSF, and miR-15a in both CSF and plasma of DCI patients have been reported [53, 48]. In other biomarker studies, the levels of miR-146a-5p, miR-17-5p, and miR-451a in whole blood were significantly different in aSAH patients compared to the HCs, but no miRNA showed statistically significant differences between CVS− and CVS− patients [34]. Su et al reported that miR-132-3p is differentially expressed in peripheral blood between DCI+ and DCI− patients [52]. The data from the selected miRNA panel were generally consistent with the findings of these prior studies. However, because the wide differences in the patient cohorts, specimens used, sampling/analysis time points, detection methodologies, and variations on study focus (e.g. aSAH vs control, occurrence of CVS or DCI, etc), it is difficult to make direct comparisons between the results and those reported in the previously published studies.

The customized and focused miRNA panel as disclosed herein provides a clinically meaningful biomarker tool for early CVS prediction, especially during a critical period in which additional and devastating neurological injury may be reduced or averted though treatment.

Example 18: Overall Prediction of 8-miRNA Panel

Table 5 presents a prediction table incorporating 8 miRNAs, including let-7b-5p, miR-142-3p, miR-15b-5p, miR-17-5p, miR-19b-3p, miR-20a-5p, miR-24-3p, and miR-29a-3p.

TABLE 5

Overall performance of CVS risk prediction of 7-miRNA panel.

| Cases | DCVS Prediction by 8-miRNA Panel | Diagnosis |
| --- | --- | --- |
| CohortC-CSF4 | No | NO |
| CohortC-CSF13 | Yes | NO |
| CohortC-CSF30 | No | NO |
| CohortC-CSF34 | No | NO |
| CohortD-CSF1 | No | NO |
| CohortD-CSF5 | No | NO |
| CohortC-CSF22 | Yes | YES |
| CohortC-CSF26 | No | YES |
| CohortD-CSF9 | Yes | YES |
| CohortD-CSF13 | Yes | YES |
| CohortD-CSF17 | Yes | YES |
| CohortD-CSF21 | Yes | YES |

CSF specimens of 12 (twelve) aSAH cases (6 new cases and 6 replicate cases) were subject to analysis using the selected 8-miRNA biomarker panel. The analysis showed that this selected panel correctly predicted 10 out of 12 cases for either DCV+ or DCV− (Table 5).

Figure 6:
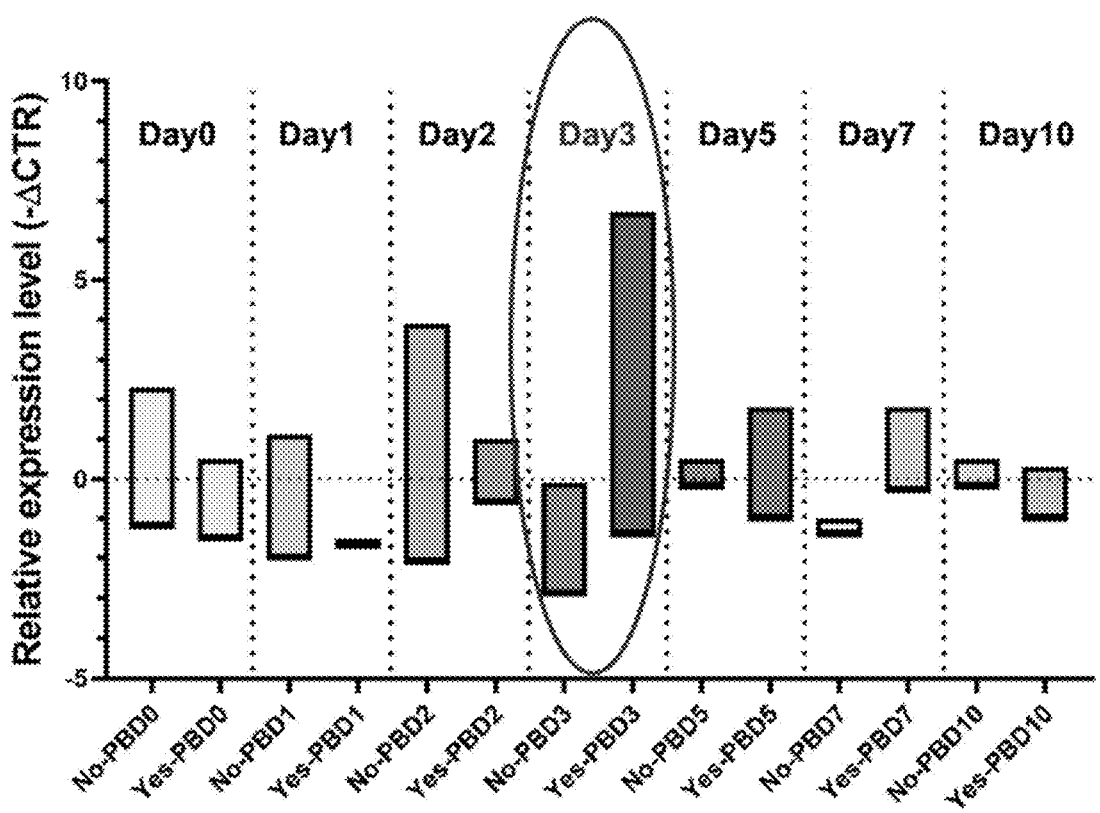
FIG. 6. The analysis of CSF specimens collected at different time points (PBD0 (8-12 hrs), PBD1, PBD2, PBD3, PBD5, PBD7, and PBD10) following aneurysm ruptured demonstrated dynamic changes of miRNA biomarker (8-miRNA) panel across the sampling time range. The greatest difference between DCV+ and DCV− was observed at PBD3, thus, PBD3 is a preferred time for specimen sampling to determine the risk of DCV. PBD: post-bleed day.

Example 19: DCVS+ vs. DCVS− Difference in Specimen Collected at Different Time Points CSF specimens were collected at various time points following aneurysm rupture: day 0 (PBD), 8-12 hrs), Day 1 (PBD1), Day 2 (PBD2), Day 3 (PBD3), Day 5 (PBD5), Day 7 (PBD7), and Day 10 (PBD10). The CSF specimens were analyzed using an 8-miRNA panel, including let-7b-5p, miR-142-3p, miR-15b-5p, miR-17-5p, miR-19b-3p, miR-20a-5p, miR-24-3p, and miR-29a-3p. With reference to FIG. 6, the greatest difference between DCV+ and DCV− was observed at PBD3, thus, PBD3 is a preferred time for specimen sampling to determine the risk of DCV. PBD: post-bleed day.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES 1. de Rooij N K, Linn F H, van der Plas J A, Algra A, Rinkel G J. Incidence of subarachnoid haemorrhage: a systematic review with emphasis on region, age, gender and time trends. J Neurol Neurosurg Psychiatry. 2007; 78(12): 1365-72. doi:10.1136/jnnp.2007.117655.
2. Bederson J B, Connolly E S, Jr., Batjer H H, Dacey R G, Dion J E, Diringer M N et al. Guidelines for the management of aneurysmal subarachnoid hemorrhage: a statement for healthcare professionals from a special writing group of the Stroke Council, American Heart Association. Stroke. 2009; 40(3):994-1025. doi:10.1161/STROKEAHA.108.191395.
3. Dority J S, Oldham J S. Subarachnoid Hemorrhage: An Update. Anesthesiol Clin. 2016; 34(3):577-600. doi: 10.1016/j.anclin.2016.04.009
4. D'Souza S. Aneurysmal Subarachnoid Hemorrhage. J Neurosurg Anesthesiol. 2015; 27(3):222-40. doi:10.1097/ANA.0000000000000130.
5. Lantigua H, Ortega-Gutierrez S, Schmidt J M, Lee K, Badjatia N, Agarwal S et al. Subarachnoid hemorrhage: who dies, and why? Crit Care. 2015; 19:309. doi:10.1186/s13054-015-1036-0.
6. Seule M, Oswald D, Muroi C, Brandi G, Keller E. Outcome, Return to Work and Health-Related Costs After Aneurysmal Subarachnoid Hemorrhage. Neurocrit Care. 2020. doi:10.1007/s12028-019-00905-2.
7. Al-Mufti F, Amuluru K, Changa A, Lander M, Patel N, Wajswol E et al. Traumatic brain injury and intracranial hemorrhage-induced cerebral vasospasm: a systematic review. Neurosurg Focus. 2017; 43(5):E14. doi:10.3171/2017.8.FOCUS17431.
8. Janjua N, Mayer S A. Cerebral vasospasm after subarachnoid hemorrhage. Curr Opin Crit Care. 2003; 9(2):113-9.
9. Brami J, Chousterman B, Boulouis G, Dorze M L, Majlath M, Saint-Maurice J P et al. Delayed Cerebral Infarction is Systematically Associated with a Cerebral Vasospasm of Large Intracranial Arteries. Neurosurgery. 2020; 86(2):E175-e83. doi:10.1093/neuros/nyz340.
10. Kolias A G, Sen J, *Belli* A. Pathogenesis of cerebral vasospasm following aneurysmal subarachnoid hemorrhage: putative mechanisms and novel approaches. J Neurosci Res. 2009; 87(1):1-11. doi:10.1002/jnr.21823.
11. Macdonald R L, Weir B K. A review of hemoglobin and the pathogenesis of cerebral vasospasm. Stroke. 1991; 22(8):971-82.
12. Dietrich H H, Dacey R G, Jr. Molecular keys to the problems of cerebral vasospasm. Neurosurgery. 2000; 46(3):517-30.
13. Carr K R, Zuckerman S L, Mocco J. Inflammation, cerebral vasospasm, and evolving theories of delayed cerebral ischemia. Neurol Res Int. 2013; 2013:506584. doi:10.1155/2013/506584.
14. Chou S H. Inflammation, Cerebral Vasospasm, and Brain Injury in Subarachnoid Hemorrhage-A Shifting Paradigm and a New Beginning. Crit Care Med. 2018; 46(11):1883-5. doi:10.1097/CCM.0000000000003373.
15. Eisenhut M. Vasospasm in cerebral inflammation. Int J Inflam. 2014; 2014:509707. doi:10.1155/2014/509707.
16. Miller B A, Turan N, Chau M, Pradilla G. Inflammation, vasospasm, and brain injury after subarachnoid hemorrhage. Biomed Res Int. 2014; 2014:384342. doi:10.1155/2014/384342.
17. Mocco J, Zacharia B E, Komotar R J, Connolly E S, Jr. A review of current and future medical therapies for cerebral vasospasm following aneurysmal subarachnoid hemorrhage. Neurosurg Focus. 2006; 21(3):E9.
18. Etminan N, Vergouwen M D, Ilodigwe D, Macdonald R L. Effect of pharmaceutical treatment on vasospasm, delayed cerebral ischemia, and clinical outcome in patients with aneurysmal subarachnoid hemorrhage: a systematic review and meta-analysis. J Cereb Blood Flow Metab. 2011; 31(6):1443-51. doi:10.1038/jcbfm.2011.7.
19. Bartel D P. MicroRNAs: genomics, biogenesis, mechanism, and function. Cell. 2004; 116(2):281-97.
20. Huntzinger E, Izaurralde E. Gene silencing by microRNAs: contributions of translational repression and mRNA decay. Nat Rev Genet. 2011; 12(2):99-110. doi:10.1038/nrg2936.
21. Liu N K, Xu X M. MicroRNA in central nervous system trauma and degenerative disorders. Physiol Genomics. 2011; 43(10):571-80. doi:10.1152/physiolgenomics.00168.2010.
22. Wang W X, Visavadiya N P, Pandya J D, Nelson P T, Sullivan P G, Springer J E. Mitochondria-associated microRNAs in rat hippocampus following traumatic brain injury. Exp Neurol. 2015; 265:84-93. doi:10.1016/j.expneurol.2014.12.018.
23. Koutsis G, Siasos G, Spengos K. The emerging role of microRNA in stroke. Curr Top Med Chem. 2013; 13(13): 1573-88.
24. Tan J R, Koo Y X, Kaur P, Liu F, Armugam A, Wong P T et al. microRNAs in stroke pathogenesis. Curr Mol Med. 2011; 11(2):76-92.
25. Wang W X, Rajeev B W, Stromberg A J, Ren N, Tang G, Huang Q et al. The expression of microRNA miR-107 decreases early in Alzheimer's disease and may accelerate disease progression through regulation of beta-site amyloid precursor protein-cleaving enzyme 1. J Neurosci. 2008; 28(5):1213-23. doi:10.1523/JNEUROSCI.5065-07.2008.
26. Wang W X, Wilfred B R, Madathil S K, Tang G, Hu Y, Dimayuga J et al. miR-107 regulates granulin/progranulin with implications for traumatic brain injury and neurodegenerative disease. Am J Pathol. 2010; 177(1):334-45. doi:10.2353/ajpath.2010.091202.
27. Vikman P, Beg S, Khurana T S, Hansen-Schwartz J, Edvinsson L. Gene expression and molecular changes in cerebral arteries following subarachnoid hemorrhage in the rat. J Neurosurg. 2006; 105(3):438-44. doi: 10.3171/jns.2006.105.3.438.
28. Muller A H, Povlsen G K, Bang-Berthelsen C H, Kruse L S, Nielsen J, Warfvinge K et al. Regulation of microRNAs miR-30a and miR-143 in cerebral vasculature after experimental subarachnoid hemorrhage in rats. BMC Genomics. 2015; 16:119. doi:10.1186/s12864-015-1341-7.
29. Li H T, Wang J, Li S F, Cheng L, Tang W Z, Feng Y G. Upregulation of microRNA24 causes vasospasm following subarachnoid hemorrhage by suppressing the expression of endothelial nitric oxide synthase. Mol Med Rep. 2018; 18(1):1181-7. doi:10.3892/mmr.2018.9050.
30. Liu D, Han L, Wu X, Yang X, Zhang Q, Jiang F. Genome-wide microRNA changes in human intracranial aneurysms. BMC Neurol. 2014; 14:188. doi:10.1186/s12883-014-0188-x.
31. Cordes K R, Sheehy N T, White M P, Berry E C, Morton S U, Muth A N et al. miR-145 and miR-143 regulate smooth muscle cell fate and plasticity. Nature. 2009; 460(7256):705-10. doi:10.1038/nature08195.

32. O'Connell R M, Rao D S, Baltimore D. microRNA regulation of inflammatory responses. Annu Rev Immunol. 2012; 30:295-312. doi:10.1146/annurev-immunol-020711-075013.
33. Khoshnam S E, Winlow W, Farbood Y, Moghaddam H F, Farzaneh M. Emerging Roles of microRNAs in Ischemic Stroke: As Possible Therapeutic Agents. J Stroke. 2017; 19(2):166-87. doi:10.5853/jos.2016.01368.
34. Lopes K P, Vinasco-Sandoval T, Vialle R A, Paschoal F M, Jr., Bastos V, Bor-Seng-Shu E et al. Global miRNA expression profile reveals novel molecular players in aneurysmal subarachnoid haemorrhage. Sci Rep. 2018; 8(1):8786. doi:10.1038/s41598-018-27078-w.
35. Tan K S, Armugam A, Sepramaniam S, Lim K Y, Setyowati K D, Wang C W et al. Expression profile of MicroRNAs in young stroke patients. PLoS One. 2009; 4(11):e7689. doi: 10.1371/journal.pone.0007689.
36. Mraz M, Malinova K, Mayer J, Pospisilova S. MicroRNA isolation and stability in stored RNA samples. Biochem Biophys Res Commun. 2009; 390(1):1-4. doi: 10.1016/j.bbrc.2009.09.061.
37. Etheridge A, Lee I, Hood L, Galas D, Wang K. Extracellular microRNA: a new source of biomarkers. Mutat Res. 2011; 717(1-2):85-90. doi:10.1016/j.mrfmmm.2011.03.004.
38. Frontera J A, Claassen J, Schmidt J M, Wartenberg K E, Temes R, Connolly E S, Jr. et al. Prediction of symptomatic vasospasm after subarachnoid hemorrhage: the modified fisher scale. Neurosurgery. 2006; 59(1):21-7; discussion—7. doi:10.1227/01.NEU.0000218821.34014.1B.
39. Kirsch J D, Mathur M, Johnson M H, Gowthaman G, Scoutt L M. Advances in transcranial Doppler US: imaging ahead. Radiographics. 2013; 33(1):E1-E14. doi: 10.1148/rg.331125071.
40. Wang W X, Fardo D W, Jicha G A, Nelson P T. A Customized Quantitative PCR MicroRNA Panel Provides a Technically Robust Context for Studying Neurodegenerative Disease Biomarkers and Indicates a High Correlation Between Cerebrospinal Fluid and Choroid Plexus MicroRNA Expression. Mol Neurobiol. 2017; 54(10): 8191-202. doi:10.1007/s12035-016-0316-2.
41. Moldovan L, Batte K E, Trgovcich J, Wisler J, Marsh C B, Piper M. Methodological challenges in utilizing miRNAs as circulating biomarkers. J Cell Mol Med. 2014; 18(3):371-90. doi:10.1111/jcmm.12236.
42. Wang W X, Danaher R J, Miller C S, Berger J R, Nubia V G, Wilfred B S et al. Expression of miR-15/107 family microRNAs in human tissues and cultured rat brain cells. Genomics Proteomics Bioinformatics. 2014; 12(1):19-30. doi:10.1016/j.gpb.2013.10.003.
43. AppliedBiosystems. Crt, a relative threshold method for qPCR data analysis on the QuantStudio™ 12K Flex system with OpenArray® technology. Appl Biosyst QuantStudio™ 12K Flex Real-Time PCR Syst Appl Note. 2016; CO28730, 4.
44. Mestdagh P, Van Vlierberghe P, De Weer A, Muth D, Westermann F, Speleman F et al. A novel and universal method for microRNA R T-qPCR data normalization. Genome Biol. 2009; 10(6):R64. doi:10.1186/gb-2009-10-6-r64.
45. Team R C. R: a language and environment for statistical computing. R Foundation for Statistical Computing, Vienna, Austria 2020.
46. Therneau T A, Beth rpart: Recursive Partitioning and Regression Trees. R package, version 4.1-15. 2019.
47. Bache S, Rasmussen R, Rossing M, Laigaard F P, Nielsen F C, Moller K. MicroRNA Changes in Cerebrospinal Fluid After Subarachnoid Hemorrhage. Stroke. 2017; 48(9):2391-8. doi:10.1161/STROKEAHA.117.017804.
48. Kikkawa Y, Ogura T, Nakajima H, Ikeda T, Takeda R, Neki H et al. Altered Expression of MicroRNA-15a and Kruppel-Like Factor 4 in Cerebrospinal Fluid and Plasma After Aneurysmal Subarachnoid Hemorrhage. World Neurosurg. 2017; 108:90916 e3. doi:10.1016/j.wneu.2017.09.008.
49. Pulcrano-Nicolas A S, Proust C, Clarencon F, Jacquens A, Perret C, Roux M et al. Whole-Blood miRNA Sequencing Profiling for Vasospasm in Patients With Aneurysmal Subarachnoid Hemorrhage. Stroke. 2018; 49(9):2220-3. doi:10.1161/STROKEAHA.118.021101.
50. Sheng B, Fang X, Liu C, Wu D, Xia D, Xu S et al. Persistent High Levels of miR-502-5p Are Associated with Poor Neurologic Outcome in Patients with Aneurysmal Subarachnoid Hemorrhage. World Neurosurg. 2018; 116:e92-e9. doi:10.1016/j.wneu.2018.04.088.
51. Stylli S S, Adamides A A, Koldej R M, Luwor R B, Ritchie D S, Ziogas J et al. miRNA expression profiling of cerebrospinal fluid in patients with aneurysmal subarachnoid hemorrhage. J Neurosurg. 2017; 126(4):1131-9. doi:10.3171/2016.1JNS151454.
52. Su W, Chan A H, Lu G, Lin M, Sze J, Zhou J Y et al. Circulating microRNA 132-3p and 324-3p Profiles in Patients after Acute Aneurysmal Subarachnoid Hemorrhage. PLoS One. 2015; 10(12):e0144724. doi:10.1371/journal.pone.0144724.
53. Powers C J, Dickerson R, Zhang S W, Rink C, Roy S, Sen C K. Human cerebrospinal fluid microRNA: temporal changes following subarachnoid hemorrhage. Physiol Genomics. 2016; 48(5):361-6. doi:10.1152/physiolgenomics.00052.2015.
54. Lu G, Wong M S, Xiong MZQ, Leung C K, Su W, Zhou J Y et al. Circulating MicroRNAs in Delayed Cerebral Infarction After Aneurysmal Subarachnoid Hemorrhage. J Am Heart Assoc. 2017; 6(4). doi:10.1161/JAHA.116.005363.
55. Lai N S, Zhang J Q, Qin F Y, Sheng B, Fang X G, Li Z B. Serum microRNAs are non-invasive biomarkers for the presence and progression of subarachnoid haemorrhage. Biosci Rep. 2017; 37(1). doi:10.1042/BSR20160480.
56. Sheng B, Lai N S, Yao Y, Dong J, Li Z B, Zhao X T et al. Early serum miR-1297 is an indicator of poor neurological outcome in patients with aSAH. Biosci Rep. 2018; 38(6). doi:10.1042/B5R20180646.
57. Bache S, Rasmussen R, Wolcott Z, Rossing M, Mogelvang R, Tolnai D et al. Elevated miR-9 in Cerebrospinal Fluid Is Associated with Poor Functional Outcome After Subarachnoid Hemorrhage. Translational Stroke Research. 2020. doi:10.1007/s12975-020-00793-1
58. Wang, W-X, et al., A Highly Predictive MicroRNA Panel for Determining Delayed Cerebral Vasospasm Risk Following Aneurysmal Subarachnoid Hemorrhage. Frontiers in Molecular Biosciences. 2021; Vol. 8, Art. 657258.
59. Wang, W-X, et al., MicroRNAs as Biomarkers for Predicting Complications Following Aneurysmal Subarachnoid Hemorrhage. *Intl. J. of Molecular Sciences*. 2021; 22, 9492.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of quantitative measurement of at least five miRNAs in a biological sample from a subject following aneurysmal subarachnoid hemorrhage (aSAH) when an intracranial arterial aneurysm ruptures, comprising:
   providing a biological sample collected from the subject about 3, 7, or 10 days following aSAH; and
   determining amounts of at least five miRNAs in the biological sample, selected from the group consisting of: let-7b-5p, miR-9-3p, miR-15b-5p, miR-17-5p, miR-19b-3p, miR-20a-5p, miR-24-3p, miR-29a-3p, miR-125b-5p, and miR-142-3p; and
   administering a hypertension medication to the subject.

2. The method of claim 1, wherein the biological sample is obtained from the subject about 3 days following aSAH.

3. The method of claim 1, and further comprising administering an intra-arterial injection of a vasodilator to the subject, wherein the hypertension medication is a vasodilator administered via intra-arterial injection to the subject.

4. The method of claim 1, wherein the hypertension medication is a vasodilator administered via intra-arterial injection to the subject.

5. The method of claim 1, and further comprising:
   (a) calculating a risk score of a patient using a statistical model and the determined amounts of the at least five miRNAs as input data, and comparing the risk score to one or both of:
   (i) a basal score that is an established score generated from a group of healthy controls who do not have aSAH or any clinically manifested neurological disease or diagnosis, and
   (ii) a low-risk score that is an established score that is generated from a group of aSAH patients who did not experience cerebral vasospasm; and
   (b) identifying the subject as having an elevated risk for developing vasospasm when the calculated risk score is higher than the basal score and/or the low-risk score.

6. The method of claim 5, and further comprising administering a hypertension medication to the subject.

7. The method of claim 5, and further comprising administering an intra-arterial injection of a vasodilator to the subject.

8. The method of claim 5, and further comprising administering nimodipine to the subject.

9. The method of claim 1, wherein the biological sample is selected from cerebrospinal fluid and plasma.

10. The method of claim 1, and further comprising administering a treatment to the subject when the elevated risk of cerebral vasospasm is identified.

11. The method of claim 10, wherein the treatment is a hypertension medication, an intra-arterial injection of a vasodilator, or a combination thereof.

12. The method of claim 11, wherein the intra-arterial injection of the a-vasodilator is intra-arterial nicardipine, verapamil, or nitroglycerin.

13. The method of claim 11, wherein the hypertension medication is a calcium channel blocker that is nimodipine.

14. The method of claim 10, wherein the biological sample is obtained from the subject about 3 days following aSAH.

15. The method of claim 10, wherein the biological sample is selected from cerebrospinal fluid and plasma.

\* \* \* \* \*